United States Patent [19]

Smith

[11] Patent Number: 5,683,987
[45] Date of Patent: Nov. 4, 1997

[54] THERAPEUTIC OLIGONUCLEOTIDES TARGETING THE HUMAN MDR1 AND MRP GENES

[75] Inventor: Larry J. Smith, Omaha, Nebr.

[73] Assignee: The Board of Regents of the University of Nebraska, Lincoln, Nebr.

[21] Appl. No.: 487,141

[22] Filed: Jun. 7, 1995

Related U.S. Application Data

[63] Continuation-in-part of Ser. No. 379,180, Jul. 12, 1994, abandoned.

[51] Int. Cl.$^6$ .................... A01N 43/04; C07H 21/02; C07H 71/04; C07H 19/04
[52] U.S. Cl. .................... 514/44; 514/44; 536/23.1; 536/24.5; 536/24.31
[58] Field of Search .................... 536/23.1, 24.5, 536/24.31; 514/44

[56] References Cited

PUBLICATIONS

Agrawal, S. et al., 1991 Proc. Natl. Acad Sci. 88: 7579–7599.
Agrawal, S. et al., 1989 Proc. Natl. Acad. Sci. USA 86: 7790–7794.
Bayever, E. et al., 1992 Antisense Res. Dev. 2: 109–110.
Biro, S. et al., 1993 Proc. Natl. Acad. Sci. USA 90: 654–658.
Chen C. et al., 1990 J. Biol. Chem. 265: 506–514.
Chin, K. 1993 Adv. Cancer Res. 60: 157–180.
Christen, R.D., et al. 1994 Cancer and Metastasis Reviews 13: 175–189.
Clark, R. et al. 1992 J. Natl. Cancer Inst. 84: 1506–1512.
Cole, S.C. et al., 1992 Science 258: 1650–1654.
Conrad, R. et al., 1994 J. Biol. Chem 269: 32051–32054.
Cornish, et al. 1993 Pharm. Comm. 3: 239–247.
Corrias, M.V. & Tonini, G.P. 1992 Anticancer Res. 12: 1431–1438.
Crooke, S.T. 1992 Ann. Rev. Pharm. Toxicol. 32: 329–376.
Efferth, T. & Volm, M. 1993 Oncology 50: 303–308.
Fan, D. et al., 1992 Anticancer Res. 12: 661–667.
Grant, C.E. 1994 Cancer Res. 54: 357–361.
Gray G.D., et al. 1993 Cancer Res. 53: 577–580.
Gupta, S. et al., 1992 J. Clin. Immunol. 12: 451–458.
Gupta, S. et al., 1994 Cancer Lett. 76: 139–145.
Higgins, K.A, et al., 1993 Proc. Natl. Acad. Sci. USA 90: 9901–9905.
Ishikawa T. et al., 1994 J. Biol. Chem 269: 29085–29093.
Iversen P., 1991 Anticancer Drug Design 6: 531–538.
Jaroszewski, J.W. et al., 1990 Cancer Commuications 2: 287–294.
Karp, J.E. & Broder, S., 1994 Cancer Res. 54: 653–665.
Kitajima et al., 1992 J. Biol. Chem. 267: 25881–25888.
Kohno et al., J. 1990 J. Biol. Chem 265: 19690–19696.
Krishnamachary, N. & Center, M.S., 1993 Cancer Res. 53: 3658–3661.
Rychlik, R. et al. 1989 Nucleic Acids Research 17: 8543–8551.
Marie, J.P. et al., 1993 Leukemia 6: 821–824.
Miller, T.P. et al., 1991 J. Clin. Oncol. 9: 17–24.
Neckers, L. et al., 1992 Critical Reviews in Oncogenesis 3: 175–231.
Papaphilis, A.D. et al., 1990 Anticancer Res. 10: 1201–1212.
Rivoltini, L. et al., 1990 Int. J. Cancer 46: 727–732.
Raderer, M. & Scheithauer, W., 1993 Cancer 72: 3553–3563.
Riordan, J.R. et al., 1985 Pharmac. Ther. 28: 51–75.
Pastan; I. d Gottesman, M. M., 1991 Ann. Rev. Med. 42: 277–286.
Schultze, P. et al., 1994 J. Mol. Biol. 235: 1532–1547.
Sonneveld, P. et al., 1992 The Lancet 340: 255–259.
Stein, C.A. et al., 1993 Biochemistry 32: 4855–4861.
Thierry, A.R. 1993 Biochem. BioPhys. Res. Comm. 190: 952–960.
Vasanthankumar, G. & Ahmed, N.K., 1989 Cancer Comm. 1: 225–232.
Ward, N.E. et al., 1995 J. Biol. Chem. 270: 8056–8060.
Wickstrom, E. et al., 1992 Cancer Res. 52: 6741–670.
Zaman, G.J., et al., 1993 Cancer Res. 53: 1747–1750.
Gravitt, K.R. et al., 1994 Biochem. Pharmacol. 48: 375–381.
Chin, J.E. et al., 1989 Mol. Cell. Biol. 9: 3808–3820.
Grunicke, H. et al., 1994 Ann. Hematol. 69: S1–S6.
Ratajczak, M.Z. et al., 1992 Proc. Natl. Acad. Sci. USA 89: 11823–11827.
Gekeler, V. et al., 1995 Biochem. Biophys. Res. Comm. 206: 119–126.

*Primary Examiner*—George G. Elliott
*Assistant Examiner*—Andrew Wang
*Attorney, Agent, or Firm*—Dann, Dorfman, Herrell and Skillman

[57] ABSTRACT

The present invention provides novel compositions and methods useful in cancer therapy for inhibiting the multidrug resistance phenotype, which often thwarts long-term chemotherapeutic regimens. The novel compositions of matter comprise oligonucleotides targeted to the human MDR1 and MRP genes, which inhibit expression of these genes, thereby rendering tumors and other forms of cancer more susceptible to the cytotoxic effects of chemotherapeutic agents. Oligonucleotides are also provided that inhibit the multidrug resistance phenotype by exerting an aptameric effect.

32 Claims, 1 Drawing Sheet

THERAPEUTIC OLIGONUCLEOTIDES TARGETING THE HUMAN MDR1 AND MRP GENES

CROSS REFERENCE TO RELATED APPLICATIONS

This is continuation-in-part of U.S. application Ser. No. 08/379,180 filed on Jul. 12, 1994, now abandoned.

FIELD OF THE INVENTION

The present invention relates to novel compositions and methods useful in cancer therapy for inhibiting the multidrug resistance phenotype, which is responsible for the failure of existing chemotherapeutic regimens to induce enduring remissions in the majority of cancer patients (Clarke et al., *J. Natl. Cancer Inst.* 84: 1506–1512, 1992). Specifically, the invention provides selected oligonucleotides (hereinafter "oligos"), and methods of use thereof, for inhibiting expression of genes responsible for the MDR phenotype, and for exerting aptameric inhibition of the MDR phenotype.

BACKGROUND OF THE INVENTION

The multidrug resistance phenotype is dependent upon the expression of molecular pumps that are capable of expelling chemotherapeutic agents from their site of action in cancer cells. These molecular pumps include, for example, the P-glycoprotein (hereinafter: P-gp) pump, and the multidrug resistance-associated protein (hereinafter: MRP) pump, which are encoded by the MDR1 and MRP genes, respectively.

The discussion set forth below illustrates the problems faced by clinical investigators seeking to improve cancer treatments. A number of references have been included to describe the general state of the art. Inclusion of these references is not an admission that such references represent prior art with respect to the present invention.

Multidrug resistance (hereinafter "MDR") is largely dependent on the expression of one or the other or both of two different genes. These genes encode transmembrane energy-dependent molecular "pumps" that expel a wide variety of anticancer agents from their site of action in tumors (Grant et al., *Cancer Res.* 54: 357–361, 1994; Riordan and Ling, *Pharmacol. Ther.* 28: 51–75, 1985). The normal functions of these molecular pumps is not well defined, but both are expressed by hematopoietic cells and P-gp has been shown to have a causal role in immunofunctioning (Gupta et al., *J. Clin. Immunol.* 12: 451–458, 1992). The MRP is a molecular pump initially found to be involved in multidrug resistance in lung cancer, and then later found to be expressed in other cancer types, while P-gp is a molecular pump long known to be involved in producing multidrug resistance in many tumor types (Chin et al., *Adv. Cancer Res.* 60: 157–180, 1993; Cole et al., *Science* 258: 1650–1654, 1992; Grant et al., *Cancer Res.* 54: 357–361, 1994; Krishnamachary and Center, *Cancer Res.* 53: 3658–3661, 1993; Zaman et al., *Cancer Res.* 53: 1747–1750, 1993).

Clinical studies in which P-gp inhibitors were administered prior to chemotherapy showed that such competitive inhibitors could increase the response of the tumors to the anticancer agents without causing an equivalent increase in toxicity to normal tissues (Marie et al., *Leukemia* 7: 821–824, 1993; Miller et al., *J. Clin. Oncol.* 9: 17–24, 1991; Pastan and Gottesman, *Annu. Rev. Med.* 42: 277–286, 1991; Raderer and Scheithauer, *Cancer* 72: 3553–3563, 1993; Sonneveld et al., *Lancet* 340: 255–259, 1992). Oligos designed to block the expression of MRP or P-gp have several features which should make them more clinically effective than any of the existing competitive inhibitors of P-gp or to any comparable inhibitors for MRP.

First, most chemical inhibitors used clinically to combat multidrug resistance have serious side effects unrelated to their ability to inhibit P-gp. In contrast, the phosphorothioate oligo, OL(1)p53, has been found to be essentially devoid of any toxicity when administered to patients (Bayever et al., *Antisense Res. Dev.* 2: 109–110, 1992; *Antisense Res. Dev.*, in press, 1994). Similarly, this and other phosphorothioates have been shown to be nontoxic to a variety of animal species, even when given at high doses (Cornish et al., *Pharmacol. Com.* 3: 239–247, 1993; Crooke, *Ann. Rev. Pharm. Toxicol.* 32: 329–376, 1992; Iversen, *Anti-Cancer Drug Design* 6: 531–538, 1991). These findings show that at least some types of oligo have no acute toxicity per se when given systemically to animals or patients.

Second, some oligos, including phosphorothioates, have been shown often to have an RNAse-H dependent mechanism of action (Crooke, *Ann. Rev. Pharm. Toxicol.* 32: 329–376, 1992). RNAse-H enzyme activity is often expressed in clonogenic cells, while little or no activity is found in differentiated (non-proliferative) cells (Papaphilis et al., *Anticancer Res.* 10: 1201–1212, 1990; Crooke, *Ann. Rev. Pharm. Toxicol.* 32: 329–376, 1992). Because of this, blocking MRP or P-gp synthesis with oligos (as opposed to blocking their function by competitive inhibitors) should be relatively more effective in proliferating than in non-proliferating cells. Most normal cells that express P-gp or MRP are non-proliferating. For example, gastrointestinal crypt cells (stem cells) do not express P-gp, whereas the endstage (non-proliferating) luminal cells do (Chin et al., *Adv. Cancer Res.* 60: 157–180, 1993). Furthermore, once MRP or P-gp synthesis is blocked, the remaining membrane-associated drug-efflux pump of the parent cell would then be divided between the two daughter cells, reducing the effective amount of the molecular pump in the proliferating tumor cell population by one-half for each population doubling.

In addition, several recent papers report that ODNs not only are capable of blocking the expression of particular genes in vitro, but also are able to produce this effect in vivo. Some groups have successfully inhibited HIV gene expression (including tax) in human cells in xenogeneic transplant models (Kitajima et al., *J. Biol. Chem.* 267:25881–25888, 1992). Others have targeted genes in cancer cells, including c-myc, c-Ha-ras, NF-kB, c-myb, c-kit and bcr-abl. In each of these instances involving the administration of ODNs to treat animals with xenogeneic human cancers, the transplanted malignant cells were found to regress (Agrawal et al., *Proc. Natl. Acad. Sci.* 86:7790–7794, 1989; *Proc. Natl. Acad. Sci.* 88:7595–7599, 1991; Biro et al., *Proc. Natl. Acad. Sci.* 90:654–658, 1993; Gray et al., *Cancer Res.* 53:577–580, 1993; Higgins et al., *Proc. Natl. Acad. Sci.* 90:9901–9905, 1993; Ratajczak et al., *Proc. Natl. Acad. Sci.* 89:11823–11827, 1992; Wickstrom et al., *Cancer Res.* 52:6741–6745, 1992).

Furthermore, the Food and Drug Administration has approved several phosphorothioate antisense oligonucleotides for systemic administration to patients and for ex vivo treatment of hematopoietic stem cell grafts. These approvals include the now-completed OL(1)p53 phase I clinical trials (both systemic and ex vivo administered) which targeted transcripts of the p53 gene in patients with acute myeloid leukemia (Bayever et al., *Antisense Res. Develop.* 2: 109–110, 1992; Karp and Broder, *Cancer Res.* 54: 653–665, 1994). Thus, antisense oligonucleotides have the pharmacologic properties necessary for use as drugs.

There are six reports claiming reduced drug resistance in cultured cell lines following treatment with oligos targeting MDR-1 mRNA. Three of these (Vasanthakumar & Ahmed, *Cancer Com.* 1: 225–232, 1989; Rivoltini et al., *Int. J. Cancer* 46: 727–732, 1990; Efferth & Volm, *Oncology* 50:303–308, 1993) are totally unconvincing because they used oligos directed against mouse MDR-1 to treat human cells; in the corresponding human MDR-1 sequence, the longest matching nucleotide sequence was only 6 bases long. The paper by Thierry et al. (*Biochem. Biophys. Res. Comm.* 190: 952–960, 1993) reports no oligo with a sequence which matches the human MDR-1 gene, but this problem is apparently due to typing errors (personal communication from A. Thierry). Thierry's 15-mer that gave 95% inhibition of MDR-1 expression did so only when encapsulated in liposomes; this was associated with a 4-fold increase in sensitivity of the tumor cells to doxorubicin (Thierry et al., *Biochem. Biophys. Res. Comm.* 190: 952–960, 1993); when administered without liposomes, inhibition of MDR1 expression was 40% of control values. Furthermore, the calculated melting temperature for Thierry's 15-mer is less than 28° C., suggesting that at body temperature the amount of oligo bound is very low.

The most compelling papers in this group are by Jaroszewski et al. (*Cancer Comm.* 2: 287–294, 1990) and Corrias and Tonini (*Anticancer Res.* 12: 1431–1438, 1992). Both teams found inhibition with only one out of five oligos. Jaroszewski et al. (*Cancer Comm.* 2: 287–294, 1990) describe one phosphorothioate (which is being designated "Cohen(1)mdr" herein) that gave 25% reduction in P-gp expression at 15 µM and 33% reduction at 30 µM when incubated with MCF-7/ADR breast cancer cells for 5 days. This reduction in P-gp expression was associated with a small increase in the doxorubicin sensitivity of the cells (20% increase in cell death when 10 µM of the oligo was used. Corrias & Tonini (*Anticancer Res.* 12: 1431–1438, 1992) report a phosphodiester oligo that gave only a slight reduction in P-gp (data not shown herein) at 30 µM when incubated with doxorubicin-resistant colon adenocarcinoma cells for 36 hours. The reduction in P-gp expression was associated with a significant increase in the in vitro sensitivity of the cells to the cytotoxic effects of doxorubicin (80% and 53% dose reductions in $IC_{50}$, respectively; the $IC_{50}$ being the inhibitory concentration of a chemotherapeutic agent (e.g., doxorubicin) which causes a 50% inhibition in cellular proliferation).

It is, therefore, a principal object of the present invention to provide MDR-oligos or MRP-oligos that target the genes encoding P-gp or MRP, respectively, or their RNA transcripts, in order to specifically and effectively sensitize clonogenic multidrug-resistant tumor cells to chemotherapeutic agents. It is another object of the present invention to provide oligos which will sensitize tumor cells much more efficiently than they do normal cells which express these same molecular pumps. As the foregoing discussion highlights, oligonucleotides effective for these purposes heretofore have been unavailable.

There is growing evidence that certain protein kinases, such as protein kinase A (PKA), and protein kinase C (PKC) in particular, are involved in the activation of the forms of drug resistance which depend on the expression of molecules producing multidrug resistance, such as, for example, P-glycoprotein, MRP, pi-class glutathione S-transferase, gamma-glutamylcysteine (Gekeler et al., *Biochem. Biophys. Res. Comm.* 205: 119, 1995; Grunicke et al., *Ann. Hematol.* 69 (Suppl 1): S1-6, 1994; Gupta et al., *Cancer Lett.* 76: 139, 1994), or the transmembrane pump capable of expelling glutathione conjugates from their site of action in cells (such as the GS-X pump (Ishikawa et al., *J. Biol. Chem.* 269: 29085, 1994).

These second-messenger pathways typically appear to be more active in drug resistant cancer cells compared to their drug sensitive counterparts. These pathways promote the expression of various drug resistance phenotypes by causing the up-regulation of a very small number of specific transcriptional regulators, including AP-1, that presumably control the activation of molecules involved in producing drug resistance in cancer cells (Grunicke et al., *Ann. Hematol.* 69(Suppl 1): S1-6, 1994). For example, activation of the ras oncogene in malignant cells is one of the ways that PKC and, in turn, multidrug resistance, can be up-regulated in tumor cells. Hence, the realization that what has been considered to be multiple discrete mechanisms for drug resistance share common activation pathways opens a new set of possibilities for broad spectrum therapeutic interventions.

Thus, if inhibitors of these second messenger pathways could be found, they should be of use for treating a wider variety of multidrug resistance phenotypes in cancer than agents designed to inhibit the function or expression of a single molecular species involved in drug resistance (Grunicke et al., *Ann. Hematol.* 69(Suppl 1): S1–6, 1994; Christen et al., *Cancer Metastasis Rev.* 13: 175, 1994). In addition, inhibitors of particular PKC isoenzymes, or of PKA, or molecular regulators up- or down-stream of these enzymes, should find a variety of other applications where these protein kinases are known to play an important role, including the treatment of viral infections, AIDS, Alzheimer's Disease, and conditions where immunosuppression is important such as in autoimmune diseases, transplantation-related reactions and inflammatory reactions.

Stein et al. (*Biochemistry* 32: 4855, 1993) discovered that both a 15-mer phosphodiester homopolymer of thymidine and a 28-mer phosphorothioate homopolymer of cytidine could inhibit the β1 isoenzyme of PKC, with the result that pinocytosis and cellular uptake of macromolecules was inhibited. For the 28-mer phosphorothioate, the $IC_{50}$ for directly inhibiting purified PKC-β1 activity was 1 µM; complete suppression required nearly 40 µM.

Conrad et al (*J. Biol. Chem.* 269: 32051, 1994) have shown that certain RNA aptamers can inhibit the βII isoenzyme of PKC. These RNA aptamers were selected from a pool of RNA molecules that contained a 120-nucleotide randomized region. PKC-βI is an alternatively-spliced variant of PKC-βII.

Schuttze et al (*J. Mol. Biol.* 235: 1532, 1994) have analyzed in detail the three-dimensional solution structure of the thrombin-binding DNA aptamer d(GGTTGGTGTGGTTGG). This aptamer binds to thrombin and inhibits its activity in the chain of reactions that lead to blood clotting. The authors conclude that "knowledge of the three-dimensional structure of this thrombin aptamer may be relevant for the design of improved thrombin-inhibiting anti-coagulants with similar structural motifs."

Using the human KM12L4a colon cancer cell line, Gravitt et al. (*Biochem. Pharmacol.* 48: 375, 1994) discovered that the agent thymeleatoxin (which stimulates the phorbol ester-responsive PKC isoenzymes -α, -βI, -βII and -gamma) induces multidrug resistance. Since this cell line expresses only the PKC-α isoenzyme, it is clear that PKC-α lies in a second messenger pathway that can up-regulate multidrug resistance.

Fan et al (*Anticancer Res.* 12: 661, 1992) presented data showing that the expression of rat brain PKC-βI confers a multidrug resistance phenotype on rat fibroblasts.

Thus, it is another object of the present invention to provide oligonucleotides that inhibit various MDR phenotypes in cancer cells by exerting an aptameric effect.

SUMMARY OF THE INVENTION

In accordance with the present invention, there are provided novel oligonucleotides targeting the human MDR1 gene or the human MRP gene or their transcripts which are uniquely effective in inhibiting multidrug resistance in human cancer cells. Administration of these oligos to patients having multidrug resistant cancer is done for the purpose of increasing sensitivity of the cancer(s) to the cytotoxic effects of therapeutic agents that would normally be expelled from their site of action in the tumor cells by the MRP or P-gp molecular pumps. In addition, the oligos may be administered to a patient with cancer or a premalignant syndrome to prevent the development of multidrug resistance in the patient's tumor. The oligos may be used alone or in combination with certain chemical inhibitors which exhibit an inhibitory effect on the MRP or P-gp pumps. The oligos may also be used in combination with chemotherapeutic drugs to purge bone marrow or peripheral stem cell grafts of malignant cells or non-malignant mononuclear cytotoxic effector cells. The oligos may be administered to patients receiving an organ transplant, or patients with autoimmune diseases, as an immunosuppressive agent alone or with other MRP or P-gp inhibitors or with cytotoxic or cytostatic drugs. The oligos to MDR1 herein described are much more effective than other oligos presently known. Oligos directed toward inhibiting expression of the MRP gene have not been described previously, insofar as is known.

Furthermore, the present inventor has found that MRP-oligos have activity for reversing multidrug resistance phenotype in non-lung cancer.

"Prototype oligos" have been designed, synthesized and used to confirm in in vitro experiments that indeed the nucleotide target sequences for oligo binding indicated in Tables 1 through 3 ("hotspots") within the MRP and MDR1 gene sequences or transcript sequences are particularly suitable for the practice of the present invention. Variant oligos with suitable physical properties have also been designed which target the same general areas of the MDR1 or MRP sequences as the prototype oligos. Such variant oligos, described herein in Tables 4 and 5 are expected to also have utility for the same therapeutic purposes as the prototype oligos.

Also disclosed are a set of oligonucleotide sequences which can dramatically reverse the multidrug resistance phenotype exhibited by cancer cells, even though the oligo sequences are such that they are not complementary to any known human gene. They must act, therefore, by interfering with the function of some key molecule needed for the production of the multidrug resistance phenotype. This type of phenomenon is generally known as an "aptameric effect." The oligonucleotides exhibiting this specific aptameric effect (hereinafter "MDR-aptamer" oligos) are highly active in vitro at concentrations below 1 μM. The degree to which these MDR-aptamers reverse the multidrug resistance phenotype is positively correlated with the degree to which, by themselves, they inhibit the in vitro proliferation of drug-resistant cancer cells. These MDR-aptamers do not have a major drug sensitizing effect on drug sensitive cells and they do not significantly inhibit the proliferation of such cells. Similarly, some MDR- and MRP-Oligos exhibit both an antisense effect on MDR1 or MRP expression and (to verying degrees) an MDR-aptameric effect. These MDR-aptamers can serve a variety of purposes, including being used: (1) to treat cancer patients, particularly those with multidrug resistant cancer, in order to sensitize the tumor to chemotherapeutic agents; (2) as probes to discover the critical molecular target in cells (to which they bind) required for the maintenance of the multidrug resistance phenotype; and (3) as prototype MDR-aptamers in structural studies for the further development of oligos of this type for clinical use as therapeutic agents.

DETAILED DESCRIPTION OF THE INVENTION

Figure 1:
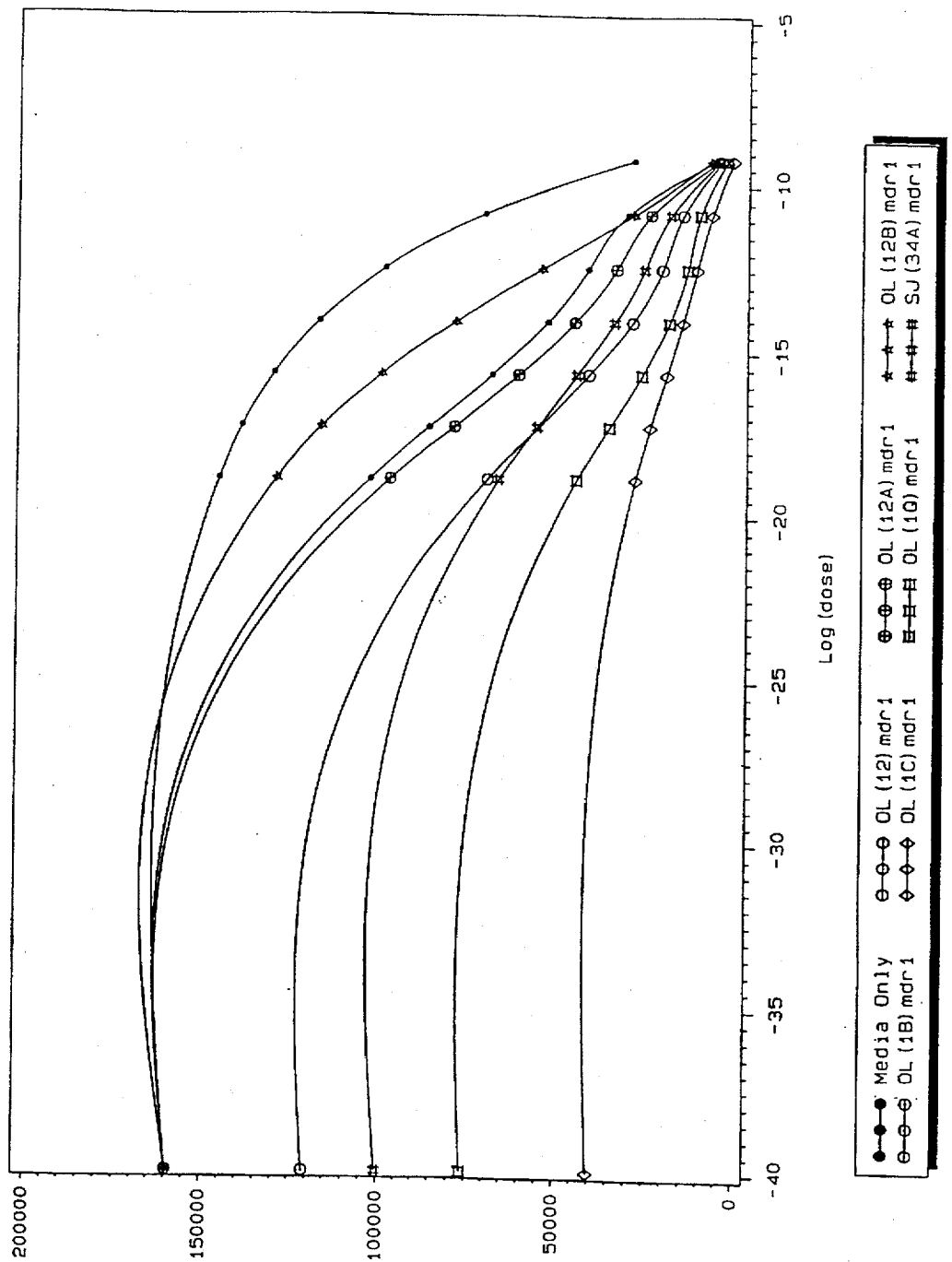
FIG. 1. Graph of predicted $^3$H-TdR uptake count (Y-axis) as a function of $Log_{10}$ (dose of drug) (X-axis) for selected mdr oligonucleotides. The graph plots the estimated functions (curved lines) associating $Log_{10}$ (Vincristine dose) with expected "$^3$H-TdR counts" for each oligo shown in the figure.

In preferred embodiments of the invention, the oligos are administered systemically to cancer patients, either in combination with chemotherapeutic agents, in order to potentiate the elimination of multidrug resistant tumor cells from the body of the host; or alone, to prevent development of multidrug resistant phenotype, or with chemotherapeutic agents to purge malignant cells from bone marrow or peripheral stem cell grafts. The oligos also may be administered as an immunosuppressive agent.

The list of chemotherapeutic agents to be used in association with the prototype or variant oligos of the present invention is selected from but not limited to a list that comprises: (1) the vinca alkaloids: including vincristine, vinblastine, vindesine; (2) the anthracyclines, including daunorubicin, doxorubicin, idarubicin; (3) the epipodophyllotoxins, including VP-16 (etoposide) and VM-26 (teniposide); and (4) miscellaneous: steroids, mitomycin C, taxol, actinomycin D, melphalan.

The prototype or variant oligos may be used alone to inhibit P-gp or MRP function, or in combination with non-oligo inhibitors of these molecular pumps, selected from but not limited to a list comprising: PSC-833 (cyclosporin D analog), verapamil, cyclosporin A, FK506, tamoxifen, megestol, and novobiocin and its analogs.

The prototype or variant oligos may be used alone or in combination with the aforementioned agents to treat any human cancer which expresses a multidrug resistant phenotype, or to prevent the development of a multidrug resistance phenotype, including those types of human cancer selected from but not limited to a list comprising: breast cancer, lung cancer, colon cancer, liver cancer, renal cancer, pancreatic cancer, prostate cancer, ovarian cancer, cervical cancer, uterine cancer, bladder cancer, brain cancer, adrenal cancer, multiple myeloma, ear-nose-throat cancers (including esophageal, laryngeal, pharynx), leukemia, lymphoma, sarcoma and carcinoid tumors. This listing is included for the purpose of illustration only, and is not meant to limit the practice of the present invention.

The present invention encompasses oligonucleotides and oligonucleotide analogs which are complementary to selected target sites of MDR1 or MRP, and transcripts thereof. These target sites are sometimes referred to herein as "hotspots." Using a computer program, such as "Oligo" (Richik & Rhoades, *Nucl. Acids Res.* 17: 8543, 1989) and a reference such a Genbank, these hotspots were selected on the basis of their unique sequence (i.e., having high sequence homology with members of the gene family, but less than 85% homology with genes and RNA transcripts outside the gene family) and various physical parameters desirable for the antisense oligonucleotides to be produced. In preferred embodiments of the invention, oligos which are targeted to these "hotspots" possess the following characteristics: (1) length between about 10 and 40 bases, with a preferred range of about 15–30 and a particularly preferred range of 17–26; (2) negligible self-interaction (self-dimers and hairpins) under physiological conditions; (3) melting temperature $\geq 40°$ C. under physiological conditions; and (4) no more than 40% of the oligo composed of run of guanines or cytosines.

Preferred hotspots, prototype oligonucleotides and size variants thereof are set forth herein. These hotspots and oligos are disclosed with reference to specific MDR1 or MRP nucleotide sequences from the Genbank library. It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, either with respect to the preferred hotspot disclosed herein or the oligos targeted to specific locations on the respective genes or RNA transcripts. With respect to the inclusion of such variants, the term "substantially the same as" is used herein to refer to various specific nucleotide sequences and variants thereof that would occur in a human population. Additionally, the term "substantially the same as" refers to oligo sequences that may not be perfectly matched to a target sequence, but the mismatches do not materially affect the ability of the oligo to hybridize with its target sequence under the conditions described.

The subject of the present invention is the nucleotide sequence of the disclosed oligos (listed in Tables 1 through 5) in association with a chemical backbone, the backbone selected from, but not limited to, a list consisting of the following types (reviewed in Neckers et al., *Crit. Rev. Oncogen.* 3: 175–231, 1992): phosphorothioates, dithioates, methylphosphonates, phosphodiesters, morpholino backbones, polyamide backbones, and any combination of the aforementioned backbone types, including, for example, phosphorothioate-capped phosphodiesters. The backbones may be unmodified, or they may be modified to incorporate a ribozyme structure, or a pendant group. Additionally, 2'-O-methyl (ribose-modified) oligos are suitable for the practice of the invention. The 2'-O-methyl sugar modification can be associated with any of the backbone linkages, including phosphorothioates, and the modification can be limited to the ends of the oligonucleotide. The oligos may also be associated with a carrier or vehicle such as liposomes or micelles, although other carriers could be used, as would be appreciated by one skilled in the art. Such carriers are used to facilitate the cellular uptake and/or targeting of the oligo, and/or improve the oligo's pharmacokinetic and/or toxicologic properties.

TABLE 1

Preferred 20-mer, 22-mer and 26-mer MDR-oligo nucleotide sequences within targeting hotspots

| SEQ ID NO. | HOT-SPOT | Nucleotide Starting Position* | OLIGO (Trivial Name) and variants of same length | OLIGO SEQUENCE (5' —> 3') | |
|---|---|---|---|---|---|
| 1 | 1 | 488 | OL(6)mdr prototype | CCCACGCCCC | GGCGCTGTTC |
| 2 |   | 496 | OL(6A)mdr | GTGCTCAGCC | CACGCCCCGG |
| 3 | 2 | 517 | OL(16)mdr prototype | GGCAAAGAGA | GCGAAGCGGC |
| 4 |   | 518 | OL(16A)mdr | TGGCAAAGAG | AGCGAAGCGG |
| 5 |   | 540 | SJ(34)mdr prototype | TCGAATGAGC | TCAGGCTTCC |
| 6 |   | 542 | SJ(34A)mdr | TCGAATGAGC | TCAGGCTT |
| 7 |   | 540 | SJ(34B)mdr | ACTCGAATGA | GCTCAGGCTT CC |
| 8 |   | 533 | SJ(34C)mdr | AGCTCAGGCT | TCCTGTGGCA |
| 9 |   | 543 | SJ(34D)mdr | CGAATGAGCT | CAGGCT |
| 10 | 3 | 664 | 5(1)mdr prototype | CCCTACCTCG | CGCTCCTTGG AACGGC |
| 11 |   | 688 | OL(10)mdr | GCTCCCAGCT | TTGCGTGCCC |
| 12 | 4 | 884 | OL(12)mdr prototype | GCGCGCTCCG | GGCAACATGG |
| 13 |   | 881 | OL(12A)mdr | CGCGCTCCGG | GCAACATGGT CC |
| 14 |   | 885 | OL(12B)mdr | CGCGCTCCGG | GCAACATG |
| 15 |   | 881 | OL(12C)mdr | CTCCGGGCAA | CATGGTCC |
| 16 |   | 941 | OL(15)mdr prototype | TGCTTCCTCC | CACCCACCGC |
| 17 |   | 937 | OL(15A)mdr | TCCTCCCACC | CACCGCCCGC |
| 18 |   | 938 | OL(15B)mdr | TTCCTCCCAC | CCACCGCCCG |
| 19 |   | 939 | OL(15C)mdr | CTTCCTCCCA | CCCACCGCCC |
| 20 |   | 940 | OL(15D)mdr | GCTTCCTCCC | ACCCACCGCC |
| 21 | 5 | 1000 | OL(5)mdr prototype | TCTGGACTTT | GCCCGCCGCC |

TABLE 1-continued

Preferred 20-mer, 22-mer and 26-mer MDR-oligo nucleotide sequences within targeting hotspots

| SEQ ID ID NO. | HOT-SPOT | Nucleotide Starting Position* | OLIGO (Trivial Name) and variants of same length | OLIGO SEQUENCE (5' —> 3') | | |
|---|---|---|---|---|---|---|
| 22 | | 1001 | OL(5A)mdr | TTCTGGACTT | TGCCCGCCGC | |
| 23 | | 1002 | OL(5B)mdr | GTTCTGGACT | TTGCCCGCCG | |
| 24 | | 1003 | OL(5C)mdr | CGTTCTGGAC | TTTGCCCGCC | |
| 25 | 6 | 1125 | OL(1)mdr prototype | GCTCCTCCAT | TGCGGTCCCC | |
| 26 | | 1123 | OL(1B)mdr | GCTCCTCCAT | TGCGGTCCCC | TT |
| 27 | | 1125 | OL(1C)mdr | TCTTTGCTCC | TCCATTGCGG | TCCCC |
| 28 | | 1125 | OL(1Q)mdr | TTTGCTCCTC | CATTGCGGTC | CCC |
| 29 | | 1125 | OL(1W)mdr | TCCTCCATTG | CGGTCCCC | |
| 30 | | 1123 | OL(1Wa)mdr | CTCCATTGCG | GTCCCCTT | |
| 31 | | 1125 | OL(1Wb)mdr | CTCCATTGCG | GTCCCC | |
| 32 | | 1121 | OL(1Wc)mdr | CCATTGCGGT | CCCCTTCA | |
| 33 | | 1127 | OL(1X)mdr | GCTCCTCCAT | TGCGGTCC | |
| 34 | | 1122 | OL(1A)mdr | CCTCCATTGC | GGTCCCCTTC | |
| 35 | 7 | 1688 | OL(2)mdr prototype | GCAACCAGCA | CCCCAGCACC | |
| 36 | | 1691 | OL(2A)mdr | GCAGCAACCA | GCACCCCAGC | |
| 37 | 8 | 5996 | OL(3)mdr prototype | TGCCCACCAG | AGCCAGCGTC | |
| 38 | | 6278 | OL(15)mdr prototype | GCCTCCTTTG | CTGCCCTCAC | GA |
| 39 | 9 | 6551 | SJ(36)mdr prototype | CCAGGGCTTC | TTGGACAACC | TA |

*The nucleotide starting position for targeting MDR1-gene transcripts is based on the GenBank entries HUMMDR1AO1 through HUMMDR1A26, considered as a single linear sequence, with Number 1 position being the most 5-prime nucleotide of the HUMMDR1AO1 GenBank entry. The Nucleotide Starting Positions in this Table represent the most 5-prime nucleotide of the corresponding sense sequence.

Particularly preferred for practice of the invention are oligos that hybridize to the hotspots listed below (or substantially equivalent variants) for MDR-1, Genbank reference No. HUMMDR1-AO1 through -AO26, taken consecutively (Chin et al., Mol. Cell. Biol. 9: 3808, 1989; Chen et al., J. Cell. Biochem. 265: 506, 1990).

Hot-spot 6:
Range of bases includes positions 1121–1158
(bases numbered as per footnote to Table 1);
sequence below (Sequence I.D. No. 102) is coding strand:
5'-TGAAGGGGACCGCAATGGAGGAGCAAAGAAGAAGAACT-3'

Hot-spot 2:
Range of bases includes positions 540–564;
sequence below (Sequence I.D. No. 103) is coding strand:
5'-GGAAGCCTGAGCTCATTCGAGTAGC-3'

Hot-spot 3:
Range of bases includes positions 685–708;
sequence below (Sequence I.D. No. 104) is coding strand:
5'-AGGGGCACGCAAAGCTGGGAGCT-3'

Hot-spot 4:
Range of bases includes positions 881–904:

-continued sequence below (Sequence I.D. No. 105) is coding strand:
5'-GGACCATGTTGCCCGGAGCGCGCA-3'

Table 1A describes several sequence variants of antisense oligos in Hotspot 3 of the MDR1 gene. Table 1B describes very similar oligos that bind near the translational start site of the mRNA. Oligo "5(1C)mdr" (SEQ ID NO:94) binds to an upstream splice junction site, while oligo "5(1G)mdr" (SEQ ID NO:98) binds to a site just upstream of the start codon. Interestingly, nearly identical sequences (only 1 base difference in 22) exist in both the genomic and the spliced cDNA versions of the gene (starting positions #666 and #405, respectively). The fourth position guanine in SEQ ID NO:98 makes a perfect match with the "AUG" start site region, while a fourth-position thymidine in SEQ ID NO:94 makes a perfect match precisely with the upstream exon 1B/intron 1 splice junction. A variant of these oligos, synthesized with a fourth position inosine base (such as, for example, oligo "5(1J)mdr", SEQ ID NO:101) should be able, therefore, to bind equally to transcripts from either site.

TABLE 1A

Additional sequence variants in the Hotspot 3 region of mdr1 gene

| SEQ ID NO. | HOT-SPOT | Nucleotide Starting Position[1] | Oligo Trivial Name | Oligo Sequence (5' —> 3') | | |
|---|---|---|---|---|---|---|
| 93 | 3 | 673 | 5(1A)mdr | CGTGCCCCTA | CCTCGCGCTC | CT |
| 93 | 3 | 666 | 5(1B)mdr | CCCTACCTCG | CGCTCCTTGG | AACG |
| 94 | 3 | 666 | 5(1C)mdr | CCCT$^2$ACCTCG | CGCTCCTTGG | AA |
| 95 | 3 | 671 | 5(1D)mdr | CGTGCCCCTA | CCTCGCGCTC | CTTG |
| 96 | 3 | 677 | 5(1E)mdr | CGTGCCCCTA | CCTCGCGC | |

TABLE 1B

Additional sequence variants in the upstream splice junction site

| SEQ ID NO. | HOT-SPOT | Nucleotide Starting Position[4] | Oligo Trivial Name | Oligo Sequence (5' → 3') | | |
|---|---|---|---|---|---|---|
| 97 | — | 408 | 5(1F)mdr | TCCCGACCTC | GCGCTCCT | |
| 98 | — | 403 | 5(1G)mdr | CCCG[2]ACCTCG | CGCTCCTTGG | AA |
| 99 | — | 405 | 5(1H)mdr | CCATCCCGAC | CTCGCGCTCC | TTGG |
| 100 | — | 403 | 5(1I)mdr | CCATCCCGAC | CTCGCGCTCC | TTGGAA |
| 101 | — | 405 | 5(1J)mdr | CCCI[3]ACCTCG | CGCTCCTTGG | |

[1]The nucleotide starting position for targeting MDR1-gene transcripts is based on the GenBank entries HUMMDR1A01 through HUMMDR1A26, considered as a single linear sequence, with Number 1 position being the most 5-prime nucleotide of the HUMMDR1A01 GenBank entry. The Nucleotide Starting Positions in this Table represent the most 5-prime nucleotide of the corresponding sense sequence.
[2]If an inosine base is placed in this fourth base position, then the resulting ODN would effectively be a perfect match with both binding sites.
[3]This variant sequence contains an inosine base substituted at the fourth position where the single-base variation between SEQ ID NO:94 and SEQ ID NO:98 exits.
[4]The nucleotide starting position for targeting mdr1 mRNA is based on GenBank entry HUMMDR1/M14758.

TABLE 2

Preferred 23-mer MDR-oligo nucleotide sequences within targeting hotspots.

| SEQ ID NO. | HOT-SPOT | Nucleotide Starting Position* | OLIGO (Trivial Name) and variants of same length | OLIGO SEQUENCE (5' → 3') | | |
|---|---|---|---|---|---|---|
| 40 | 10 | 670 | PA(1)mdr prototype | GCGGGAGGTG | AGTCACTGTC | TCC |
| 41 | | 670 | AP(1)mdr | GGAGACAGTG | ACTCACCTCC | CGC |

*The nucleotide starting position for targeting the MDR1-gene is based on the GenBank Entry J05674: "Hummdr1B", and represents the most 5-prime nucleotide of the corresponding sense sequence.

TABLE 3

Preferred 20-mer and 26-mer MRP-oligo nucleotide sequences within targeting hotspots

| SEQ ID NO. | HOT-SPOT | Nucleotide Starting Position* | OLIGO (Trivial Name) and variants of same length | OLIGO SEQUENCE (5' → 3') | | |
|---|---|---|---|---|---|---|
| 42 | 1 | 24 | 5(3)MRP prototype | CGGCGGCGGC | GGCGCAGGGA | GCCGGG |
| 43 | 2 | 169 | 5(2)MRP prototype | CGGTGGCGCG | GGCGGCGGCG | GGCACC |
| 44 | 3 | 220 | OL(14)MRP prototype | GCGGGTCGGA | GCCATCGGCG | |
| 45 | | 222 | OL(14A)MRP | GAGCGGGTCG | GAGCCATCGG | |
| 46 | | 223 | OL(14B)MRP | AGAGCGGGTC | GGAGCCATCG | |
| 47 | | 225 | OL(14C)MRP | CCAGAGCGGG | TCGGAGCCAT | |
| 48 | 4 | 1210 | OL(5)MRP prototype | CTGCGGCCCG | GAAAACATCA | |
| 49 | 5 | 2114 | OL(2)MRP prototype | CGGTGATGCT | GTTCGTGCCC | |
| 50 | | 2101 | OL(2A)MRP | CGTGCCCCCG | CCGTCTTTGA | |
| 51 | | 2102 | OL(2B)MRP | TCGTGCCCCC | GCCGTCTTTG | |
| 52 | | 2103 | OL(2C)MRP | TTCGTGCCCC | CGCCGTCTTT | |
| 53 | | 2104 | OL(2D)MRP | GTTCGTGCCC | CCGCCGTCTT | |
| 54 | | 2105 | OL(2E)MRP | TGTTCGTGCC | CCCGCCGTCT | |
| 55 | | 2106 | OL(2F)MRP | CTGTTCGTGC | CCCCGCCGTC | |
| 56 | | 2107 | OL(2G)MRP | GCTGTTCGTG | CCCCCGCCGT | |
| 57 | | 2108 | OL(2H)MRP | TGCTGTTCGT | GCCCCCGCCG | |
| 58 | | 2109 | OL(2I)MRP | ATGCTGTTCG | TGCCCCCGCC | |
| 59 | | 2110 | OL(2J)MRP | GATGCTGTTC | GTGCCCCCGC | |
| 60 | 6 | 2516 | OL(6)MRP prototype | GGGCCAGGCT | CACGCGCTGC | |
| 61 | | 2519 | OL(6A)MRP | GCCCGGGCCA | GGCTCACGCG | |
| 62 | 7 | 2848 | OL(3A)MRPprototype | CCCTGGACCG | CTGACGCCCG | |
| 63 | | 2834 | OL(3A)MRP | CGCCCGTGAC | CCCGTTCTCC | |
| 64 | 8 | 3539 | OL(8)MRP prototype | GCGGGATGAT | GATGGCGGCG | |
| 65 | | 3538 | OL(8A)MRP | CGGGATGATG | ATGGCCGCGA | |
| 66 | | 3540 | OL(8B)MRP | GGCGGGATGA | TGATGGCGGC | |
| 67 | | 3541 | OL(8C)MRP | GGGCGGGATG | ATGATGGCGG | |
| 68 | | 3542 | OL(8D)MRP | GGGGCGGGAT | GATGATGGCG | |
| 69 | | 3543 | OL(8E)MRP | AGGGGCGGGA | TGATGATGGC | |
| 70 | | 3528 | OL(8F)MRP | ATGGCGGCGA | TGGGCGTGGC | |
| 71 | | 3529 | OL(8G)MRP | GATGGCGGCG | ATGGGCGTGG | |
| 72 | | 3530 | OL(8H)MRP | TGATGGCGGC | GATGGGCGTG | |

TABLE 3-continued

Preferred 20-mer and 26-mer MRP-oligo nucleotide sequences within targeting hotspots

| SEQ ID NO. | HOT-SPOT | Nucleotide Starting Position* | OLIGO (Trivial Name) and variants of same length | OLIGO SEQUENCE (5' —> 3') | |
|---|---|---|---|---|---|
| 73 | | 3531 | OL(8I)MRP | ATGATGGCGG | CGATGGGCGT |
| 74 | | 3532 | OL(8J)MRP | GATGATGGCG | GCGATGGGCG |
| 75 | | 3533 | OL(8K)MRP | TGATGATGGC | GGCGATGGGC |
| 76 | 9 | 4154 | OL(4)MRP prototype | CGATGCCGAC | CTTTTCTCC |
| 77 | | 4160 | OL(4A)MRP | GCCCCACGAT | GCCGACCTTT |
| 78 | | 4161 | OL(4B)MRP | CGCCCCACGA | TGCCGACCTT |
| 79 | | 4162 | OL(4C)MRP | CCGCCCCACG | ATGCCGACCT |
| 80 | | 4163 | OL(4D)MRP | TCCGCCCCAC | GATGCCGACC |
| 81 | 10 | 4933 | 3(3)MRP prototype | TGGCGGTGGC | TGCTGCTTTG |
| 82 | | 4936 | 3(3A)MRP | GGATGGCGGT | GGCTGCTGCT |
| 83 | | 4937 | 3(3B)MRP | CGGATGGCGG | TGGCTGCTGC |
| 84 | 11 | 4637 | OL(15)MRP prototype | CCGGTGGGCG | ATGGTGAGGA CG |

*The nucleotide starting position for targeting MRP-gene transcripts is based on the GenBank Entry #L05628: HUMMRPX", and represents the most 5-prime nucleotide of the corresponding sense sequence.

Particularly preferred for practice of the invention are oligos that hybridize to the hotspots listed below (or substantially equivalent variants thereof) for MRP, Genbank reference No. HUMMRPX/LO5628 (Cole et al., Science 258: 1650, 1992).

Hot-spot 1:
Range of bases includes positions 3528–3566
(numbered as per footnote to Table 3);
Sequence below (Sequence I.D. No. 106) is coding strand:
5'-GCCACGCCCATCGCCGCCATCATCATCCCGCCCTTGGC-3'

Hot-spot 2:
Range of bases includes positions 2469–2538;
sequence below (Sequence I.D. No. 107) is coding strand:
5'-CGGACAGAGATTGGCGAGAAGGGCGTGAACCTGTCT-GGGGGCCAGAAGCAGCGCGTGAGCCTGGCCCGGG-3'

Hot-spot 3:
Range of bases includes positions 1198–1242;
sequence below (Sequence I.D. No. 108) is coding strand:
5'-TCCACGACCTGATGATGTTTTCCGGGCCGCAGATCTTAAAGTTGC-3'

Hot-spot 4:
Range of bases includes positions 2805–2896;
sequence below (Sequence I.D. No. 109) is coding strand:
5'-GCCAGCACAGAGCAGGAGCAGGATGCAGAGGAGAACGGGGTCACGGGCGTCA-GCGGTCCAGGGAAGGAAGCAAAGCAAATGGAGAATGGGAT-3'

TABLE 4

Preferred Size Variants of MDR-Oligos at different starting positions in the MDR1 gene sequence hotspots

| HOT-SPOT | Nucleotide starting position | Oligo Size Variants (nucleotide length)* |
|---|---|---|
| 1 | 460 | 25.24.23.22 |
| | 461 | 25.24.23.22 |
| | 462 | 25.24.23.22 |
| | 463 | 25.24.23.22.21 |
| | 464 | 25.24.23.22.21 |
| | 465 | 25.22.21.19 |
| | 466 | 25.21.19 |
| | 467 | 25.19.18 |
| | 468 | 25.19.18.17 |
| | 469 | 25.18.17 |
| | 470 | 17 |
| | 486 | 17 |
| | 488 | 20 |
| | 496 | 20.17 |
| | 497 | 17 |
| | 498 | 17 |
| 2 | 517 | 25.24.23.22.21.20.19.18.17 |
| | 518 | 25.24.23.22.21.20.19.18 |
| | 519 | 24.23.22.21.19.18 |
| | 520 | 24.23.22.21 |
| | 521 | 22.21 |
| | 522 | 21 |

TABLE 4-continued

Preferred Size Variants of MDR-Oligos at different starting positions in the MDR1 gene sequence hotspots

| HOT-SPOT | Nucleotide starting position | Oligo Size Variants (nucleotide length)* |
|---|---|---|
|  | 523 | 21 |
| 2 | 540 | 25,24,23,22,21,20,19,18 |
|  | 541 | 23,22,21,20,19,18 |
|  | 542 | 22,21,20,19,18 |
| 3 | 663 | 25.24.23.22.21.19 |
|  | 664 | 26.25.24.23,22.21.19.18 |
|  | 665 | 25.24.23.22.21.17 |
|  | 666 | 25.24.23 |
|  | 667 | 25.24.23 |
|  | 668 | 25.24.23.22 |
|  | 669 | 25.24.23.22 |
|  | 670 | 25.24.23.22.21 |
|  | 671 | 23.21 |
|  | 672 | 23.21 |
|  | 673 | 21 |
|  | 674 | 21 |
|  | 676 | 19 |
|  | 677 | 18 |
|  | 678 | 17 |
|  | 680 | 21.19.18.17 |
|  | 681 | 19.18.17 |
|  | 682 | 19.18.17 |
|  | 683 | 21.18.17 |
|  | 684 | 21.17 |
|  | 685 | 21 |
|  | 686 | 21.17 |
|  | 687 | 21.19.17 |
|  | 688 | 17 |
| 4 | 879 | 25,24,23,22 |
|  | 880 | 24,23,22 |
|  | 881 | 23,22 |
|  | 882 | 22 |
|  | 883 | 21 |
|  | 884 | 20 |
|  | 885 | 19 |
|  | 912 | 21.19.18 |
|  | 913 | 19.18 |
|  | 914 | 19.18 |
|  | 915 | 18 |
|  | 937 | 25.24.23.22.21.20,19.18.17 |
|  | 938 | 25.24.23.22.21.20,19.18.17 |
|  | 939 | 25,24,23,22.21,20,19.18.17 |
|  | 940 | 25.24.23.22.21.20,19.18.17 |
|  | 941 | 25,24,23,22.21,20,19.18.17 |
|  | 942 | 24.23.22.21.19.18.17 |
|  | 943 | 24.23.22.21.19.18.17 |
|  | 944 | 22.21 |
|  | 945 | 21.19.18 |
|  | 946 | 19.18 |
|  | 947 | 19.17 |
| 5 | 981 | 22.21.19.18.17 |
|  | 982 | 21.19 |
|  | 983 | 19 |
|  | 984 | 19 |
|  | 985 | 18 |
|  | 986 | 17 |
|  | 995 | 23.22.19.18.17 |
|  | 996 | 22.18.17 |
|  | 997 | 17 |
|  | 998 | 19.18.17 |
|  | 999 | 24.23.22.18.17 |
|  | 1000 | 24.23.22.21.20,19.18.17 |
|  | 1001 | 22.21.20.19.18.17 |
|  | 1002 | 21.20.19.18.17 |
|  | 1003 | 20.19.18.17 |
|  | 1004 | 19.18.17 |
|  | 1005 | 24.23.19.18 |
|  | 1006 | 23.18 |
|  | 1008 | 25.24.23 |
|  | 1009 | 25.24.23 |
|  | 1010 | 25.24.23 |
|  | 1011 | 25.24.23 |

TABLE 4-continued

Preferred Size Variants of MDR-Oligos at different starting positions in the MDR1 gene sequence hotspots

| HOT-SPOT | Nucleotide starting position | Oligo Size Variants (nucleotide length)* |
|---|---|---|
|  | 1012 | 25.24.23 |
|  | 1013 | 25.24.23 |
|  | 1014 | 25.24.23 |
|  | 1015 | 25.23 |
|  | 1031 | 22.21 |
|  | 1032 | 21.19 |
|  | 1033 | 19.18.17 |
|  | 1034 | 19.17 |
|  | 1055 | 17 |
|  | 1088 | 25 |
|  | 1089 | 25 |
|  | 1090 | 25 |
|  | 1091 | 25 |
|  | 1092 | 25 |
|  | 1093 | 25 |
|  | 1094 | 25 |
| 6 | 1121 | 25.24.23.22.21.19.18.17 |
|  | 1122 | 25.24.23.22.21.20.19.18.17 |
|  | 1123 | 25.24.23.22.21.20.19.18.17 |
|  | 1124 | 25.24.23.22.21.19.18.17 |
|  | 1125 | 25.24.23.22.21.20.19.18.17 |
|  | 1126 | 25.24.23.22.21.20.19.18.17 |
|  | 1127 | 25.24.23.22.21.19.18.17 |
|  | 1128 | 25.24.23.22.21.19.18.17 |
|  | 1129 | 25.24.23.22.21.19.18.17 |
|  | 1130 | 25.24.23.22.21.19.18.17 |
|  | 1131 | 25.24.23.22.21.19 |
|  | 1132 | 25.24.23.22 |
|  | 1133 | 25.24.23 |
|  | 1134 | 25.24.23 |
|  | 1135 | 24.23 |
|  | 1136 | 24.23 |
| 7 | 1685 | 25.24.23.22.21.19.18 |
|  | 1686 | 25.24.23.22.21.19.18.17 |
|  | 1687 | 25.24.23.22.21.19.18.17 |
|  | 1688 | 25.24.23.22.21.20.19.18.17 |
|  | 1689 | 25.24.23.22.21.18 |
|  | 1690 | 25.24.23.22.21.19.18.17 |
|  | 1691 | 25.24.23.22.21.20.19.18.17 |
|  | 1692 | 25.24.23.22.21.19.18.17 |
|  | 1693 | 25.24.23.22.19.18.17 |
|  | 1694 | 25.24.23.22.19.18.17 |
|  | 1695 | 25.24.23.22.18.17 |
|  | 1696 | 24.23.22 |
|  | 1697 | 24.23 |
| 8 | 5932 | 17 |
|  | 5995 | 22.21 |
|  | 5996 | 21.20.19.18 |
|  | 5997 | 19.18.17 |
|  | 5998 | 18.17 |
|  | 5999 | 17 |
|  | 6004 | 21 |
|  | 6007 | 17 |
| 8A | 6277 | 23 |
|  | 6278 | 22,21 |
|  | 6279 | 21,20 |
|  | 6280 | 20 |
| 9 | 6548 | 24.23.22 |
|  | 6549 | 23.22 |
|  | 6550 | 22 |
|  | 6551 | 22 |
|  | 6560 | 21 |
|  | 6562 | 19 |
|  | 6563 | 18 |
|  | 6564 | 17 |

*The numbers indicate the 26-mers, 25-mers, 24-mers, etc., down to 17-mers that are contained within the oligo sequence shown. Size reduction in individual oligos is limited to removal of nucleotides from the 5-prime end only of the oligo shown at each nucleotide starting position.

TABLE 5

Preferred Size Variants of MRP-Oligos at different starting positions in the MRP gene sequence hotspots

| HOT-SPOTS | Nucleotide starting position | Oligo Size Variants |
|---|---|---|
| 1 | 20 | 17 |
|  | 21 | 17 |
|  | 22 | 17 |
|  | 24 | 26 |
|  | 36,39,42,45,48,51,54 | 25.24.23.22.21.19.18.17 |
|  | 37,40,43,46,49,52 | 25.24.23.22.21.19.18.17 |
|  | 38,41,44,47,50,53 | 25.24.23.22.21.19.18.17 |
|  | 55 | 25 |
|  | 56 | 25 |
|  | 57 | 25 |
| 2 | 169 | 26.19.18.17 |
|  | 170 | 18.17 |
|  | 171 | 17 |
| 3 | 219 | 19 |
|  | 220 | 25.24.23.22.21.20.19 |
|  | 221 | 24.23.22.21.19 |
|  | 222 | 23.22.21.20.19.18.17 |
|  | 223 | 22.21.20.19.18.17 |
|  | 224 | 21.19.18 |
|  | 225 | 20.19.18 |
|  | 226 | 19.18 |
|  | 227 | 18 |
|  | 236 | 19 |
|  | 263 | 25.24 |
|  | 264 | 25.24 |
| 4 | 1198 | 24 |
|  | 1199 | 24.23 |
|  | 1200 | 24.23 |
|  | 1201 | 24.23 |
|  | 1202 | 25.24.23.22 |
|  | 1203 | 24.23.22 |
|  | 1204 | 25.24.23.22 |
|  | 1205 | 25.24.23.22.21 |
|  | 1206 | 25.24.23.22.21 |
|  | 1207 | 25.24.23.22.21 |
|  | 1208 | 25.24.23.22.21 |
|  | 1209 | 25.23.22.21 |
|  | 1210 | 25.22.21.20.19.17 |
|  | 1211 | 25.21.17 |
|  | 1212 | 25.21.17 |
|  | 1213 | 24.21.18.17 |
|  | 1214 | 25.17 |
|  | 1215 | 25.17 |
|  | 1216 | 25.17 |
|  | 1217 | 25.17 |
| 5 | 2101 | 25.24.23.21.20.19.18.17 |
|  | 2102 | 25.24.23.21.20.19.18.17 |
|  | 2103 | 25.24.23.21.20.19.19.17 |
|  | 2104 | 25.24.23.21.20.19.18.17 |
|  | 2105 | 25.24.23.21.20.19.18.17 |
|  | 2106 | 25.24.23.21.20.19.18.17 |
|  | 2107 | 25.24.23.22.21.20.19.18.17 |
|  | 2108 | 25.24.23.22.21.20.19.18.17 |
|  | 2109 | 24.23.22.21.20.19.18.17 |
|  | 2110 | 23.22.21.20.19.18.17 |
|  | 2111 | 22.21.19.18 |
|  | 2112 | 22.21.19 |
|  | 2113 | 21 |
|  | 2114 | 20 |
|  | 2115 | 19 |
| 6 | 2469 | 25.24.23 |
|  | 2470 | 25.24.23 |
|  | 2471 | 25.24.23 |
|  | 2472 | 25.24.23.22 |
|  | 2473 | 25.24.23.22.21 |
|  | 2474 | 25.24.23.22.21 |
|  | 2475 | 25.24.23.22.21 |
|  | 2476 | 24.23.22.21 |
|  | 2477 | 23.22.21 |
|  | 2478 | 22.21 |
|  | 2479 | 21 |
|  | 2489 | 22.21 |
|  | 2490 | 21 |
|  | 2516 | 20.17 |
|  | 2517 | 17 |
|  | 2518 | 19.18.17 |
|  | 2519 | 20.19.18.17 |
|  | 2520 | 18.17 |
|  | 2521 | 17 |
| 7 | 2805 | 25 |
|  | 2829 | 25.24.23.22.21 |
|  | 2830 | 24.23.22.21 |
|  | 2831 | 23.22.21 |
|  | 2832 | 22.21.19 |
|  | 2833 | 21.19 |
|  | 2834 | 20.19 |
|  | 2935 | 19.18 |
|  | 2836 | 18 |
|  | 2837 | 18.17 |
|  | 2848 | 20.19.18.17 |
|  | 2849 | 19.18 |
|  | 2850 | 18 |
|  | 2862 | 24.23.22,21.19 |
|  | 2863 | 25.24.23.22 |
|  | 2864 | 25.24.23.22 |
|  | 2865 | 25.24.23.22 |
|  | 2866 | 24.23.22 |
|  | 2867 | 24.23 |
|  | 2868 | 24.23 |
|  | 2869 | 24.23 |
|  | 2870 | 25.24.23 |
|  | 2871 | 25.24.23 |
|  | 2872 | 24.23 |
|  | 2873 | 23 |
| 8 | 3528 | 25.24.23.22.21.20.19.18.17 |
|  | 3529 | 25.24.23.22.21.20.19.18.17 |
|  | 3530 | 25.24.23.22.21.20.19.18.17 |
|  | 3531 | 25.24.23.22.21.20.19.18.17 |
|  | 3532 | 25.24.23.22.21.20.19.18.17 |
|  | 3533 | 25.24.23.22.21.20.19.18.17 |
|  | 3534 | 25.24.23.22.21.19.18 |
|  | 3535 | 25.24.23.22.21.19.18 |
|  | 3536 | 25.24.23.22.21.19.18 |
|  | 3537 | 25.24.23.21.19 |
|  | 3538 | 25.24.23.22.21.20.19.18 |
|  | 3539 | 25.24.23.22.21.20.19.18 |
|  | 3540 | 25.24.23.22.21.20.19.18 |
|  | 3541 | 24.23.22.21.20.19.18 |
|  | 3542 | 23.22.21.20.19.18 |
|  | 3543 | 22.21.20.19.18 |
|  | 3544 | 21.19.18 |
|  | 3545 | 21.19 |
|  | 3546 | 19 |
|  | 3547 | 19.18 |
|  | 3548 | 18 |
| 9 | 4146 | 25.24.23.22 |
|  | 4147 | 24.23.22 |
|  | 4148 | 23.22.21 |
|  | 4149 | 22.21.19 |
|  | 4150 | 21.19 |
|  | 4151 | 25.24.23.22.21.19.18 |
|  | 4152 | 25.24.23.22.21.19.18 |
|  | 4153 | 25.24.23.22.21.19.18 |
|  | 4154 | 25.24.23.22.21.20.19 |
|  | 4155 | 25.24.23.22.19 |
|  | 4156 | 25.24.23.22 |
|  | 4157 | 25.24.23.22.21 |
|  | 4158 | 25.24.23.22.21.19 |
|  | 4159 | 24.23.22.21.19 |
|  | 4160 | 23.22.21.20.19.18 |
|  | 4161 | 22.21.20.19.18 |
|  | 4162 | 21.20.19.18 |
|  | 4163 | 20.19.18.17 |
|  | 4164 | 19.18.17 |

TABLE 5-continued

Preferred Size Variants of MRP-Oligos at different starting positions in the MRP gene sequence hotspots

| HOT-SPOTS | Nucleotide starting position | Oligo Size Variants |
|---|---|---|
|  | 4165 | 19.18.17 |
|  | 4166 | 18.17 |
|  | 4167 | 17 |
|  | 4173 | 17 |
| 10 | 4873 | 25 |
|  | 4929 | 25.24.23.22 |
|  | 4930 | 25.24.23.22.21 |
|  | 4931 | 25.24.23.22.21.19 |
|  | 4932 | 25.24.23.22.21.19 |
|  | 4933 | 24.23.22.21.20.19.18 |
|  | 4934 | 23.22.21.19.18 |
|  | 4935 | 22.21.19.18 |
|  | 4936 | 21.20.19.18 |
|  | 4937 | 20.19.18 |
|  | 4938 | 19.18 |
|  | 4939 | 19 |
|  | 4940 | 17 |
| 11 | 4633 | 25,24,23,22,21 |
|  | 4634 | 24,23 |
|  | 4635 | 23 |
|  | 4636 | 22,21,20,19,18 |
|  | 4637 | 21 |
|  | 4639 | 19 |
|  | 4640 | 19,18 |

Use of Selected Oligonucleotides for Systemic Treatment of Patients

Pursuant to the invention, oligos designed to inhibit the expression of the MDR1 or MRP genes are administered to patients in accordance with any of a number of standard routes of drug administration. For example, the oligo may be administered to a patient by continuous intravenous administration for a period of time such as ten days. An infusion rate of 0.05–0.5 mg/kg/hr should be suitable for the practice of the invention. Alternatively, the oligo may be injected daily, given orally or be released into the patient's body from an implanted depot or be given by some other route of administration as deemed appropriate according to the criteria of standard clinical practice.

Other inhibitors of P-gp or MRP function may be given in conjunction with the administration of the oligonucleotide in accordance with the best mode of use for the given agent. If a patient has cancer or a premalignant syndrome and the purpose of administering the oligo to the patient is to improve chemotherapy response, then chemotherapeutic agents will be given either during or at about the same time as the oligo administration. A period of about one week prior to or following the administration of the oligo should be a period of time during which chemotherapeutic drugs should be given to the patient. If the patient has cancer or a premalignant syndrome and the purpose of administering the oligo is to prevent the development of multidrug resistance in the diseased cells, then the oligos will be administered to patients at times when the patient does not have active levels of chemotherapeutic drugs in the patient's body. If a patient has an autoimmune disease, such as arthritis, is experiencing graft rejection or graft-versus-host disease, then the oligos may be administered to the patient alone or in combination with other agents including inhibitors of P-gp or MRP as an immunosuppressive therapy. Oligo doses and schedules suitable for cancer patients also should be suitable for patients with autoimmune disease or who are experiencing graft rejection. Drugs cytotoxic or cytostatic to cells of the patient's immune system may also be given in conjunction with the oligo to bring about an immunosuppressed state in the patient for the purpose of reversing the pathological conditions.

Use of Selected Oligonucleotides for Depleting Malignant Cells or Cytotoxic mononuclear cells from Bone Marrow or from Peripheral Stem Cell Harvests Pursuant to the invention, one first obtains a sample of bone marrow or peripheral stem cells in accordance with any of a number of standard techniques. The patient to receive an autologous transplant may then be treated with an optimal dose of radiation and/or chemotherapy according to standard clinical procedures.

The bone marrow or peripheral stem cell sample may be cryopreserved and stored until needed, or immediately treated with the oligo.

In order for the tumor cell or normal mononuclear cell targets to be affected by the oligo, the cells must be exposed to the oligos under conditions that facilitate their uptake by the malignant cells. This may be accomplished by a number of procedures, including, for example, simple incubation of the cells with an optimal concentration of the oligo in a suitable nutrient medium for a period of time suitable to achieve a significant reduction in P-gp or MRP expression. Four days should be sufficient incubation period, but time may need to be extended, e.g., for slow growing tumors. At this time, a chemotherapeutic drug may be added that will kill any cancer cells present in the graft in the case of an autologous transplant or non-malignant mononuclear cells that can produce graft-versus-host disease in the case of an allogeneic transplant. After the bone marrow or peripheral stem cells have been cultured as just described, they are then infused into the transplant recipient to restore hemopoiesis.

Aptameric Oligonucleotides Capable of Reversing Multidrug Resistance Phenotype The MDR-aptameric oligonucleotides shown in Table 14 (Example 7) are very active in reversing the multidrug resistance phenotype, and in inhibiting the growth of multidrug resistant cancer cells. They have little or no drug sensitizing or proliferation-inhibiting activity on drug sensitive cells. This aptameric effect also is shared by the OL(1C)mdr oligo and, to a lesser extent, by the OL(1Q)mdr and SJ(34)mdr oligos. It has been found, using a previously described technique involving purified rat brain protein kinase C isoenzymes (Ward et al., *J. Biol. Chem.* 270: 8056, 1995) that these aptameric oligonucleotides do not significantly alter the activity of PKC-α, -β or -gamma. The existing data support the concept of developing these aptamers for clinical use, using basically the same strategy described herein for oligonucleotides targeting MDR1 or MRP. Using methodology of the type described by Schultze et al (J. Mol. Biol. 235: 1532, 1994), common structural features in these aptamers can be uncovered that would provide a basis for designing additional (and perhaps more specific and more active) aptamers for reversing multidrug resistance. In addition, using standard molecular biological techniques such as those described in standard texts such as, for example, *Current Protocols in Molecular Biology* (FM Ausubel et al., eds, New York: John Wiley & Sons, Inc., 1994), these MDR-aptameric oligonucleotides can be used to identify the target molecule to which they bind and produce the effect seen on multidrug resistance.

For example, these MDR-aptamers can be radiolabeled and incubated in vitro with cells which are then lysed; or, the MDR-aptamers can be used to treat cell lysates, and fractionation studies can then be carried out to isolate molecules to which the radiolabeled MDR-aptamer binds. Studies would then be carried out to confirm that a particular molecule to which the MDR-aptamer had been tightly bound has a functional role in multidrug resistance. For example, it might be shown that the molecule to which the MDR-aptamer binds is more active, or is expressed at higher levels, in multidrug resistant cells than in the drug-sensitive counterparts.

Purification of the protein to which the aptamers bind would allow microsequencing. The protein sequence can be used to generate a set of oligonucleotide probes that can be used to identify the cDNA and/or gene sequence that encodes the said protein. If it is a known protein or gene, then this information will identify the target of the MDR-aptamers. If it is not a known gene, then the gene can be cloned and characterized. Antisense oligos against this gene would be expected to have activity in reversing multidrug resistance. Even if the gene encoding the protein to which the MDR-aptamers bind is not novel, then observation that targeting this protein with aptameric oligos leads to a reversal of the multidrug resistance phenotype is a novel observation, and it provides the basis for a new therapeutic strategy for the treatment of cancer.

In sum, preferred embodiments of the present invention relate to the systemic administration of an oligonucleotide capable of inhibiting the expression of one or more of these pumps in the tumors of patients with cancer; or administering two oligos, one capable of inhibiting, for example, P-gp expression and the other inhibiting, for example, MRP expression, thereby rendering the patient's tumor more susceptible to the cytotoxic effects of chemotherapeutic agents administered together with the oligo. Also, these oligos may be administered to patients prophylactically to prevent the development of multidrug resistance in a tumor. These oligos may be used alone to inhibit multidrug resistance, or in combination with other inhibitors of P-gp or MRP. The invention also includes procedures and compositions for ex vivo administration to purge malignant cells from bone marrow grafts. Said oligos may also be administered to transplant or autoimmune patients as immunosuppressive agents.

In another application, these oligos may be used to interrupt the blood brain barrier, thus allowing therapeutic agents to pass from the general circulation into the central nervous system.

In yet another application, MRP oligos may be of use in inhibiting the transport of leukotrienes across cell membranes, and may be of clinical use in situations where this class of compounds is involved, for example, in inflammatory/allergic responses.

Also revealed are prototype oligos that can inhibit various multidrug resistance phenotypes in cancer cells by an aptameric effect.

The following examples are provided to describe the invention in further detail. These examples are intended to illustrate, and not to limit, the invention.

EXAMPLE 1

Sensitization of multidrug-resistant (MDR+) cancer cell lines to doxorubicin by MDR-oligos.

Multidrug resistant tumor cells were incubated with 15 µM of OL(6)mdr oligo, Cohen(1)mdr oligo or a negative-control (HIV-2) oligo for 4 days at 37° C. in a humidified incubation chamber. Varying doses (5-fold serial dilutions) of doxorubicin (from $1\times10^{-5}$M to $1\times10^{-8}$M) were then added to the culture wells after the cells had been subcultured into media without oligos; cells were then incubated in the same culture environment for an additional three days. Radiolabeled (tritiated) thymidine was added to all cultures for 24 hr before harvest. Each data point is the mean of 4 replicates. The data (Table 6) demonstrate that OL(6)mdr is able to sensitize multidrug-resistant cancer cells to chemotherapeutic agents, nearly three times better than the best MDR-oligo reported in the literature (Jarozewski et al.: Cancer Comm. 2: 287–294, 1990.).

TABLE 6

Sensitization of 8226/Dox cells to killing by doxorubicin following incubation with OL(6)mdr MDR-oligo.

| Treatment | SEQ ID NO. | $IC_{50}$ dose ($\times10^{-7}$ M) | Relative Sensitization (fold increase) |
|---|---|---|---|
| Medium only | — | 6.5 | — |
| HIV-2 control oligo* | 85 | 7.0 | — |
| Cohen(1)mdr oligo** | 86 | 5.0 | 1.3 |
| OL(6)mdr oligo | 1 | 1.8 | 3.6 |

*HIV-2 nucleotide sequence (20-mer): 5'-TGTCTCCGCT TCTTCCTGCC-3' (SEQ ID NO: 85);
Cohen(1)mdr nucleotide sequence (15-mer): 5'-GCTCCTCCAT TGCGG-3' (SEQ ID NO: 86)

EXAMPLE 2

Sensitization of multidrug-resistant 8226/Dox human myeloma cells and CEM/VBL10 human leukemia cells to Vincristine following incubation with MDR-oligos under low oxygen levels.

As shown in this example, several oligos which target the MDR1 gene are able to sensitize multidrug-resistant cell lines to the cytotoxic effects of the chemotherapeutic agent Vincristine. Tumor cells were treated in vitro with 10 µM of the indicated oligo for 4 days at 37° C., then counted, dispensed into individual tubes, and pulsed with Vincristine at various doses (serial 5-fold dilutions) for 3 hrs. The cells were then washed and seeded into 96-well plates (quadruplicate replicates) for pulsing with tritiated thymidine 3 days later. Cells were harvested the next day (=4th day after drug treatment). Tritiated thymidine uptake was analyzed by liquid scintillation.

The Prototype MDR-oligos shown in Tables 1 and 2 represent the most potent of the MDR-oligos screened on the tumor cell line in these studies. In experiments not shown, most of the other phosphorothioate MDR-oligos evaluated in vitro (sequences not listed) had little-to-no capacity to sensitize targeted tumor cells to cytotoxic drugs at concentrations at which the prototype oligos had substantial activity, confirming that the dramatic antisense effects noted above were not merely a cellular response to exposure to phosphorothioate molecules, but appear to be sequence dependent.

The OL(1)mdr oligo (Table 7) is clearly much more potent than OL(6)mdr in sensitizing 8226/Dox cells to chemotherapeutic agents. Given the data in Tables 6 and 7, it is also evident that OL(1)mdr is much more potent than the Cohen(1)mdr oligo, even though the OL(1)mdr and Cohen (1)mdr oligos have overlapping sequences:

| | |
|---|---|
| OL(1)mdr | 5'-GCTCCTCCAT TGCGGTCCCC-3' (SEQ ID NO. 25) |
| Cohen(1)mdr | 5'-GCTCCTCCAT TGCGG-3' (SEQ ID NO. 86) |

The present inventor, therefore, has made the unobvious discovery that the inclusion of the sequence ("TCCCC") to the oligos that bind in the same general area as the Cohen (1)mdr oligo greatly increases the potency of the oligos in terms of sensitizing cells that express MDR1 to chemotherapeutic agents.

TABLE 7

Sensitization of multidrug-resistant tumor cells to killing by Vincristine following incubation with several MDR-oligos in 5% oxygen

| Cell Type | Oligo Used | SEQ ID NO. | IC$_{50}$ dose (×10$^{-7}$M)* | Relative sensitization (fold increase) |
|---|---|---|---|---|
| 8226/Dox | Control | — | 4.5 | — |
| | OL(1)mdr | 25 | 0.027 | 167 |
| | PA(1)mdr | 40 | 0.28 | 16 |
| | 5(1)mdr | 10 | 1.80 | 2.5 |
| | OL(6)mdr | 1 | 2.20 | 2.5 |
| CEM/ VLB10 | Control | — | 100.0 | — |
| | 5(1)mdr | 10 | 0.9 | 111 |
| | OL(6)mdr | 1 | 1.2 | 83 |
| | OL(5)mdr | 21 | 1.5 | 67 |
| | OL(1)mdr | 25 | 1.6 | 62 |
| | SJ(36)mdr | 39 | 1.6 | 62 |
| | OL(2)mdr | 35 | 1.6 | 62 |
| | PA(1)mdr | 40 | 1.9 | 53 |
| | OL(3)mdr | 37 | 2.0 | 50 |

*IC$_{50}$ = inhibitory concentration which gives 50% reduction in tritiated thymidine uptake into DNA

EXAMPLE 3

As shown in this example, it was determined that there was an increase in sensitivity of multidrug-resistant 8226/Dox human myeloma cells to Vincristine with increasing time of incubation following initial exposure to Vincristine. The experimental conditions were identical to those utilized in obtaining the data shown in Table 7, except that the present experiment had two additional time points.

TABLE 8

Increase in sensitivity of multidrug-resistant 8226/Dox human myeloma cells to Vincristine with increasing time of incubation following initial exposure to Vincristine

| Oligo Used (Trivial Name) | SEQ ID NO. | Oligo Concentration (μM) | Relative Sensitization (fold increase) | | |
|---|---|---|---|---|---|
| | | | Day 5* | Day 7 | Day 9 |
| 5(1)mdr | 10 | 2 | 3.4 | 26.9 | 724 |
| | | 10 | 2.1 | 20.5 | 423 |
| OL(1)mdr | 25 | 2 | 18.3 | 412 | 5500 |
| | | 10 | 75.8 | 389 | 5729 |
| PA(1)mdr | 40 | 2 | 2.3 | 27 | 1309 |
| | | 10 | 6.3 | 28 | 550 |
| OL(6)mdr | 1 | 2 | 1.6 | 3.5 | 61 |
| | | 10 | 1.8 | 15.9 | 550 |
| Control Oligo** | 87 | 2 | 1.0 | 0.9 | 0 |
| | | 10 | 0.8 | 7.0 | 26.2 |
| | | | IC$_{50}$ Value on: | | |
| | | | Day 5 | Day 7 | Day 9 |
| Media Control | — | | 4.4 × 10$^{-7}$ M | 7 × 10$^{-6}$ M | 5.5 × 10$^{-4}$ M |

*Days after initial treatment exposure with Vincristine
**Control oligo sequence: 5'-CCTCGGTCCC CCCTCGTCCC C-3' (SEQ ID NO. 87)

EXAMPLE 4

In vitro sensitization of MRP-expressing lung cancer cells to etoposide by MRP-oligos.

The Prototype MRP-ODN shown in Table 3 represent the most potent of the MRP-ODNs screened on the tumor cell line in these studies. The human non-small-cell lung adenocarcinoma cell line A427 was treated with oligos at various concentrations for 4 days in vitro. The cells then were pulsed with various concentrations of etoposide (range 1.6×10$^{-4}$ to 1×10$^{-6}$M) for 3 hrs. Next, cells were trypsinized and seeded by volume into 96-well plates with 12 replicates per treatment condition. Three days later, tritiated thymidine was added and the cells harvested the next day.

The OL(8)MRP antisense oligo specific to an MRP gene-related sequence, made the A427 lung cancer cell line 18-times more sensitive in vitro to the cytotoxic effects of etoposide (VP-16). The data (Table 9) confirm the specificity of this activity. OL(6)mdr, which targets transcripts of the MDR1 gene, was used as a negative control with this MRP-expressing cell line. When novobiocin, a putative MRP inhibitor, was used at the same time as VP-16, it increased the A427 drug sensitivity by about 5 fold.

TABLE 9

A427 Lung Cancer Cell Line Treated with MRP-oligos

Etoposide (VP-16)

| Treatment | SEQ ID NO. | Oligo Level (μM) | IC$_{50}$ | Relative Sensitization (fold increase) |
|---|---|---|---|---|
| Experiment 1 | | | | |
| Media Control | — | — | 3.6 × 10$^{-5}$ M* | — |
| Novobiocin | — | — | 0.72 × 10$^{-5}$ M | 5.0 |
| OL(6)mdr control | 1 | 10.0 | 2.2 × 10$^{-5}$ M | 1.6 |
| OL(6)mdr control | 1 | 5.0 | 3.0 × 10$^{-5}$ M | 1.2 |
| OL(6)mdr control | 1 | 2.5 | 4.8 × 10$^{-5}$ M | 0 |
| OL(8)MRP | 64 | 10.0 | 2 × 10$^{-6}$ M | 18.0 |
| OL(8)MRP | 64 | 5.0 | 1.0 × 10$^{-5}$ M | 3.6 |
| OL(8)MRP | 64 | 2.5 | 1.8 × 10$^{-5}$ M | 2.0 |
| Experiment 2 | | | | |
| Media Control | — | — | 5 × 10$^{-5}$ M | — |
| OL(6)MRP | 60 | 10.0 | 6 × 10$^{-6}$ M | 8 |
| 5(2)MRP | 43 | 10.0 | 8 × 10$^{-6}$ M | 6 |
| OL(3)MRP | 62 | 10.0 | 9 × 10$^{-6}$ M | 5 |
| 5(3)MRP | 42 | 10.0 | 1 × 10$^{-5}$ M | 5 |
| Experiment 3 | | | | |
| Media Control | — | — | 6.0 × 10$^{-5}$ M | — |
| OL(5)MRP | 48 | 10 | 1.0 × 10$^{-5}$ M | 6 |
| OL(14)MRP | 44 | 10 | 1.9 × 10$^{-5}$ M | 3 |
| OL(2)MRP | 49 | 10 | 2.5 × 10$^{-5}$ M | 2.4 |
| Experiment 4 | | | | |
| OL(6)mdr control | 1 | 1 | 5.0 × 10$^{-5}$ M | 0 |
| OL(4)MRP | 76 | 1 | 1.6 × 10$^{-5}$ M | 3 |

*IC$_{50}$ = inhibitory concentration which gives 50% reduction in tritiated thymidine uptake

EXAMPLE 5

In this example, experimental conditions were identical to those utilized in obtaining the data in Example 2. These data show that the MRP-oligo, OL(8)MRP, can substantially sensitize non-lung cancer cells to chemotherapeutic agents, as determined in in vitro assays.

TABLE 10

In vitro sensitization of 8226/Dox cells to Vincristine by an MRP-oligo and comparison to several MDR-ODNs for relative potency.

| Treatment | SEQ ID NO. | IC$_{50}$ dose (×10$^{-7}$ M) | Relative Sensitization (fold increase) |
|---|---|---|---|
| Medium only | — | 11 | — |
| OL(8)MRP | 60 | 0.55 | 20 |
| OL(1)mdr | 25 | 0.2 | 55 |
| OL(6A)mdr | 2 | 0.88 | 12.5 |
| OL(3)mdr | 37 | 1.0 | 11 |
| OL(2)mdr | 35 | 3.0 | 3.7 |

EXAMPLE 6

In vitro testing of MDR-Oligonucleotides was done on the multidrug-resistant (MDR+) RPMI-8226/Dox4 human multiple myeloma cell line (gift of Dr. William Dalton, Univ. Arizona Cancer Ctr., Tucson). Cells were incubated in vitro for 4 days at 37° C. with MDR-oligos at 0.2 μM final concentration; pulsed 18 hr with serial 5-fold dilutions of chemotherapeutic drug (vincristine) from 1×10$^{-4}$M to 2×10$^{-10}$M. Cells were then washed, and incubated for an additional 4 days. Tritiated thymidine ($^{3}$H-TdR) was added for last 18 hr to measure status of cellular proliferation. Controls included MDR$^{+}$ 8226 cells similarly treated with vincristine but pretreated either with (a) control ODNs, or (b) culture medium only.

TABLE 11a

MDR-ODNs

| Oligo Name | SEQ ID No. | 5'-end target site | Oligo length No. of bases) | Why the site was selected (Footnote #) | Relative Activity |
|---|---|---|---|---|---|
| OL(1)mdr | 25 | 1125[1] | 20 | | +++ |
| OL(1A)mdr | 34 | 1122 | 20 | variant | ++ |
| OL(1B)mdr | 28 | 1123 | 22 | variant | +++++ |
| OL(1C)mdr | 27 | 1125 | 25 | variant | +++++++ |
| OL(1Q)mdr | 28 | 1125 | 23 | variant | ++++++ |
| OL(1W)mdr | 29 | 1125 | 18 | variant | +++++ |
| OL(1Wa)mdr | 30 | 1123 | 18 | variant | ++++ |
| OL(1Wb)mdr | 31 | 1125 | 18 | variant | ++++ |
| OL(1Wc)mdr | 32 | 1121 | 18 | variant | ++++ |
| OL(1X)mdr | 33 | 1127 | 18 | variant | +++ |
| OL(2)mdr | 35 | 1688 | 20 | | + |
| OL(3)mdr | 37 | 5996 | 20 | | + |
| OL(5)mdr | 21 | 1000 | 20 | | +++ |
| OL(6)mdr | 1 | 488 | 20 | | + |
| OL(6A)mdr | 2 | 496 | 20 | variant | — |
| OL(7)mdr | 110 | 2199 | 20 | | + |
| OL(8)mdr | 111 | 5722 | 20 | | — |
| OL(9)mdr | 112 | 3881 | 20 | | — |
| OL(10)mdr | 11 | 688 | 20 | | +++ |
| OL(11)mdr | | 851 | 20 | | + |
| OL(12)mdr | 12 | 884 | 20 | | +++ |
| OL(12A)mdr | 13 | 881 | 22 | variant | +++++ |
| OL(12B)mdr | 14 | 885 | 18 | variant | +++ |
| OL(12C)mdr | 15 | 881 | 18 | variant | ++ |
| OL(13)mdr | | 958 | 20 | | — |
| OL(14)mdr | | 5713 | 20 | | — |
| OL(15)mdr | 16 | 941 | 20 | | — |
| OL(16)mdr | 3 | 517 | 20 | | + |
| SJ(1)mdr | 113 | 85 | 20 | splice junction | — |
| SJ(2)mdr | 114 | 673 | 20 | splice junction | ++ |
| SJ(6)mdr | | 2559 | 20 | splice junction | + |
| SJ(18)mdr | | 6074 | 20 | splice junction | + |
| SJ(30)mdr | | 4887 | 20 | splice junction | — |
| SJ(33)mdr | | 349 | 20 | splice junction | — |
| SJ(34)mdr | 5 | 540 | 20 | splice junction | +++ |
| SJ(34A)mdr | 6 | 542 | 18 | variant | +++++ |
| SJ(34B)mdr | 7 | 540 | 22 | variant | ++ |
| SJ(34C)mdr | 8 | 533 | 20 | variant | + |
| SJ(34D)mdr | 9 | 543 | 16 | variant | + |
| SJ(35)mdr | | 1097 | 20 | splice junction | — |
| SJ(36)mdr | 39 | 6551 | 22 | splice junction | + |
| 3(1)mdr | | 7051 | 20 | 3'-end | — |
| 5(1)mdr | 10 | 664 | 26 | 2, AUG start | ++ |
| 5(2)mdr | | 640 | 28 | 2 | — |
| AP(1)mdr | 41 | 670 | 23 | 3; TR binding | + |
| AP(4)mdr | | 636 | 22 | 3; TR binding | + |
| PA(1)mdr | 40 | — | 23 | reverse of AP(1) | + |
| TH(2)mdr | | 2954 | 20 | published | + |
| CAP(2)mdr | | 556 | 22 | cap site | + |
| LOW(3)mdr | | 11 | 20 | low Tm | + |
| Cohen(1)mdr | 86 | 1130 | 15 | published | + |
| NF-kB(1)mdr | | 296 | 22 | 3; TR binding | — |

TABLE 11a-continued

MDR-ODNs

| Oligo Name | SEQ ID No. | 5'-end target site | Oligo length No. of bases) | Why the site was selected (Footnote #) | Relative Activity |
|---|---|---|---|---|---|
| CAT(L)mdr | | 432 | 20 | TR binding | — |
| Y-box-mdr | | 464 | 22 | TR binding | — |

Reactivity: — = no effect; + = weak positive effect; ++++++ = very strong positive effect.
The relative reactivity indicated for each MDR-ODN summarizes results obtained with 8226/Dox4, 8226/Dox6 and CEM/VLB10 multidrug-resistant cell lines.
[1]The numbering for the 5'-end target site is based on Genbank entry HUMMDR1A01-through-HUMMDR1A26 (Chin et al., Mol. Cell. Biol. 9: 3808, 1989; Chen et al., J. Biol. Chem. 265: 506, 1990), considered as a continuous sequence with the nucleotide at the extreme 5'-end of the sequence being given the nucleotide base number 1.
[2]These ODNs were designed to have sufficient binding affinity to the 5'-untranslated portion of the cDNA to potentially block the movement of the ribosome toward the AUG start site.
[3]Binding sites of these oligos are within an enhancer for the MDR1 gene, the sequence of which is reported by Kohno et al., J. Biol. Chem. 265: 19690, 1990. (GenBank entry #HUMMDR1B/J05674).
[4]OL(7)mdr Sequence ID No. 110 TAGCCACATGGCCCCAGGAA
OL(8)mdr Sequence ID No. 111 ACTGACTTGCCCCACGGCCA
OL(9)mdr Sequence ID No. 112 CCAAAGGGCAAAGGGCAAGG
SJ(1)mdr Sequence ID No. 113 GTACCTTACCTTTTATCTGG
SJ(2)mdr Sequence ID No. 114 TGCCCCTACCTCGCGCTCCT

TABLE 11b

MRP-ODNs

| Oligo Name | SEQ ID No. | 5'-end target site[1] | ODN length (No. of bases) | Why the site was selected (Footnote #) | Relative Activity |
|---|---|---|---|---|---|
| A(1)MRP | | 1941 | 20 | AUG start site | — |
| OL(2)MRP | 49 | 2114 | 20 | | — |
| OL(3)MRP | 62 | 2848 | 20 | | +++ |
| OL(4)MRP | 76 | 4154 | 20 | | — |
| OL(5)MRP | 48 | 1210 | 20 | | + |
| OL(6)MRP | 60 | 2516 | 20 | | + |
| OL(7)MRP | | 3155 | 20 | | — |
| OL(8)MRP | 64 | 3539 | 20 | | +++++ |
| OL(9)MRP | | 3800 | 20 | | + |
| OL(10)MRP | | 4484 | 20 | | ++ |
| OL(11)MRP | | 4715 | 20 | | — |
| OL(12)MRP | | 89 | 20 | | — |
| OL(13)MRP | | 129 | 20 | | — |
| OL(14)MRP | 44 | 220 | 20 | | + |
| OL(15)MRP | 84 | 3312 | 20 | | — |
| OL(16)MRP | | 1580 | 20 | | — |
| 3(2)MRP | | 4836 | 20 | 3'-end | — |
| 3(3)MRP | 81 | 4933 | 20 | 3'-end | — |
| 5(2)MRP | 43 | 184 | 26 | 2 | +++ |
| 5(3)MRP | 42 | 24 | 26 | 2 | ++ |
| LOW(1)MRP | | 351 | 20 | low $T_m$ | — |
| LOW(2)MRP | | 714 | 20 | low $T_m$ | + |
| CAP(2)MRP | | 1 | 19 | Cap site | + |

Reactivity: — = no effect; + = weak positive effect; +++++ = strong positive effect.
[1]The numbering for the 5'-end target site is based on Genbank entry HUMMRPX/L05628 (Cole et al., Science 258: 1650, 1992) with the nucleotide at the extreme 5'-end of the sequence being given the nucleotide base number 1.
[2]These ODNs were designed to have sufficient binding affinity to the 5'-untranslated portion of the cDNA to potentially block the movement of the ribosome toward the AUG start site.

TABLE 12

IC$_{50}$ SUMMARY
(based on 8226/Dox4 human myeloma cells)

| Oligos* (trivial name) | SEQ ID NO. | Sequence Position | Oligo Length | Vincristine IC$_{50}$ | Fold-Increase in sensitivity to drug treatment** |
|---|---|---|---|---|---|
| Media Control | — | — | — | $1.2 \times 10^{-5}$ M | — |
| OL(1)mdr | 25 | 1125 | 20 | $1.4 \times 10^{-7}$ M | 86 |
| OL(1B)mdr | 26 | 1123 | 22 | $1.6 \times 10^{-8}$ M | 7500 |
| OL(1C)mdr | 27 | 1125 | 25 | $\ll 1.6 \times 10^{-9}$ M | $\gg 7500$ |
| OL(1Q)mdr | 28 | 1125 | 23 | $<1.6 \times 10^{-9}$ M | >7500 |
| OL(1W)mdr | 29 | 1125 | 18 | $2.1 \times 10^{-9}$ M | 5714 |
| OL(10)mdr | 11 | 688 | 20 | $3.0 \times 10^{-7}$ M | 40 |
| OL(12)mdr | 12 | 884 | 20 | $6.0 \times 10^{-8}$ M | 200 |
| OL(12A)mdr | 13 | 881 | 22 | $3.2 \times 10^{-8}$ M | 375 |
| OL(12B)mdr | 14 | 885 | 18 | $3.0 \times 10^{-7}$ M | 40 |
| SJ(34)mdr | 5 | 540 | 20 | $4.1 \times 10^{-8}$ M | 293 |
| SJ(34A)mdr | 6 | 542 | 18 | $<1.6 \times 10^{-9}$ M | >7500 |
| SJ(34C)mdr | 8 | 533 | 20 | $5.5 \times 10^{-9}$ M | 2182 |

*All oligonucleotides were tested at a final concentration of 0.2 μM
**Fold increase in drug sensitivity compared to media control (no oligo or drug).

EXAMPLE 7

Mathematical/statistical model used to analyze ODN- and drug-testing data

The following mathematical/statistical model was used to analyze the effects of oligos and various drug treatments on targeted tumor cells in these studies. The model is based on experiments which generally involve treatment of tumor cells with one of several ODNs or media only, and with several dose levels of an anti-cancer agent (such as, for example, vincristine (VCR)) or media only. Analysis goals were to model the relationship of cell kill to the dose of VCR (for example), and to compare the effects of the various ODNs.

Investigation of the data indicate that the logarithm of counts can be modelled as a function of the dose of drug for each ODN; i.e.:

$$\ln (\text{count}) = f(\text{dose}) + \text{error}$$

A "full model" that fits for each ODN and drug dose in a given experiment is as follows:

$$\ln (\text{count}) = \alpha + \beta_1 (\text{drug}) + \beta_2 (\text{dose}) + \beta_3 (\text{square root of dose}) + \beta_4 (\text{fourth root of dose}) + \text{error}$$

Thus, the natural log (count) is modelled as a linear function of powers of drug dose in the assay. For a fixed ODN, i, the expected count for media-only (no drug) is $$E(\text{count})_{media} = \exp (\alpha_i)$$

For the drug dose, d*, on the other hand, the expected count is $$E(\text{count})_{d^*} = \exp (\alpha_i + \beta_{2,i} d^* + \beta_{3,i} [\text{square root of } d^*] + \beta_{4,i} \{\text{fourth root of } d^*\})$$

Using standard linear regression techniques, the "full" model (19 regressor variables) was fitted to the data from all serial-dilution drug dose levels together; from this, a more parsimonious model was developed by removing regressor variables which did not contribute to the model fit. This final model contained 10 regressor variables.

From this most parsimonious model, with its 10 predictor variables, graphs of the data are prepared, in which Predicted $^3$H-TdR uptake Counts (on the Y-axis) are plotted against $Log_{10}$(dose of drug) (X-axis); this most parsimonious model fits the data with an excellent correlation coefficient of $R^2=0.98$. The estimated functions (curved lines) associating $Log_{10}$(Vincristine dose) with expected "$^3$H-TdR Counts" for each oligo can be calculated, and are shown in the following FIGURE, where the "Media only" control counts are placed on the left-hand Y-axis.

Various estimates of parameters from the parsimonious model are shown in TABLE 13, which contains the model estimate of the count for each ODN with media only; differences here (when compared to "media only" [no ODN]) reflect the cell kill associated with the ODN alone. TABLE 13 also contains an estimate of $IC_{50}$ values, the dose of vincristine (VCR) which is estimated to produce an expected count which is exactly half that expected with "media only" [no VCR]. While formal statistical comparisons of the $IC_{50}$ values of the various ODNs is not possible, an ordering of the ODNs by estimated $IC_{50}$ values is possible.

TABLE 13

Estimated Mean Count at VCR Dose = 0 and $IC_{50}$ for Oligonucleotides used to treat 8226/Dox4 cells: Results from most parsimonious model

| Oligo-nucleotide (trivial name) | SEQ ID NO. | Estimated Mean Count (cpm) | Estimated $IC_{50}$ | Fold Increase in drug sensitivity** |
|---|---|---|---|---|
| Media only | — | 159,500 | $1.28 \times 10$–5 M | — |
| OL(12)mdr | 12 | 159,500 | $5.50 \times 10$–8 M | 233 |
| OL(12B)mdr | 14 | 159,500 | $7.39 \times 10$–7 M | 17.3 |
| OL(12A)mdr | 13 | 159,500 | $2.97 \times 10$–8 M | 414 |
| OL(1B)mdr | 26 | 120,800 | $1.79 \times 10$–8 M | 715 |
| OL(1C)mdr | 27 | 40,200 | $1.33 \times 10$–7 M | 96.2 |

TABLE 13-continued

Estimated Mean Count at VCR Dose = 0 and $IC_{50}$ for Oligonucleotides used to treat 8226/Dox4 cells: Results from most parsimonious model

| Oligo-nucleotide (trivial name) | SEQ ID NO. | Estimated Mean Count (cpm) | Estimated $IC_{50}$ | Fold Increase in drug sensitivity** |
|---|---|---|---|---|
| OL(1Q)mdr | 28 | 76,200 | $1.92 \times 10$–8 M | 667 |
| SJ(34A)mdr | 6 | 100,300 | $6.81 \times 10$–8 M | 188 |

**fold increase in drug sensitivity compared to corresponding oligo control (no drug)

TABLE 14

Sensitization of 8226/Dox Cells to Killing by VCR Following Incubation with MDR-aptameric oligonucleotides

| Treatment | SEQ ID No. | Sequence (5' —> 3') | $IC_{50}$ | Fold Increase in Drug Sensitization** |
|---|---|---|---|---|
| Media | — | — | $4 \times 10$–5 M | — |
| MDR-APT-1 | 88 | CCCCTGGCGT TACCTCCTCG TTTCT | $1 \times 10$–9 M | 40,000 |
| MDR-APT-2 | 89 | TTCGCCTGAT TTCCGCCTCC CGTCT | $2 \times 10$–9 M | 20,000 |
| MDR-APT-3 | 90 | CGGTCCGTTA TGTTCCTG | $7 \times 10$–9 M | 5,714 |
| MDR-APT-4 | 91 | ACTCGCCTCC CACGTAGTGC TT | <$1 \times 10$–9 M | >40,000 |

**Fold increase in drug sensitivity compared to media control

It will be appreciated that changes may be made in the nature, composition, operation and arrangement of the various elements described herein without departing from the spirit and scope of the invention as set forth in the following claims.

What is claimed is:

1. An oligonucleotide between 15 and 30 nucleotides in length, inclusive, having a sequence that specifically hybridizes in a human cell with a complementary sequence of a human MDR1 gene and allelic variants thereof to inhibit expression of a multidrug resistance phenotype exhibited by said cell, said complementary sequence being selected from the group consisting of Sequence ID Nos: 103, 104 and 105.

2. The oligonucleotide of claim 1, which is between about 17 and about 26 nucleotides in length.

3. The oligonucleotide of claim 1, which is phosphorothioate-modified.

4. The oligonucleotide of claim 1, which specifically hybridizes to said MDR1 gene, consisting of a sequence selected from the group consisting of Sequence ID Nos: 1, 2, 3, 4, 5, 6, 7, 8, 9, 10, 11, 12, 13, 14, 15, 16, 17, 18, 19, 20, 21, 22, 23, 24, 35, 36, 37, 38, 39, 40, 92, 93, 94, 95, 96, 97, 98, 99, 100 and 101.

5. The oligonucleotide of claim 4, selected from the group consisting of Sequence ID Nos: 1, 5, 6, 8, 10, 11, 12, 13, 14, and 40.

6. An oligonucleotide between 15 and 30 nucleotides in length, inclusive, said oligonucleotide having a sequence that is fully complementary to and hybridizes with a sequence selected from the group consisting of Sequence ID Nos: 103, 104 and 105.

7. An oligonucleotide between 15 and 30 nucleotides in length, inclusive, said oligonucleotide having a sequence that specifically hybridizes with a complementary sequence of the MDR1 gene and allelic variants thereof said oligonucleotide being selected from the group consisting of Sequence ID Nos: 1, 2, 3, 4, 5, 6, 7, 8, 9, 10, 11, 12, 13, 14, 15, 16, 17, 18, 19, 20, 21, 22, 23, 35, 36, 37, 38, 39, 40, 92, 93, 94, 95, 96, 97, 98, 99, 100 and 101.

8. The oligonucleotide of claim 7, selected from the group consisting of Sequence ID Nos: 1, 5, 6, 8, 10, 11, 12, 13, 14, and 40.

9. The oligonucleotide of claim 7, which is between 17 and 27 nucleotides in length, inclusive.

10. The oligonucleotide of claim 7, which is phosphorothioate-modified.

11. An oligonucleotide between 15 and 30 nucleotides in length, inclusive, consisting of a sequence that specifically hybridizes in a human cell with a complementary sequence of a human MRP gene and allelic variants thereof to inhibit expression of a multidrug resistance phenotype exhibited by said cell, said complementary sequence being selected from the group consisting of Sequence ID Nos: 106, 107, 108 and 109.

12. The oligonucleotide of claim 11, which is between 17 and 26 nucleotides in length inclusive.

13. The oligonucleotide of claim 11, which is phosphorothioate-modified.

14. The oligonucleotide of claim 11, consisting of a sequence which specifically hybridizes with said MRP gene and allelic variants thereof selected from the group consisting of Sequence ID Nos: 42, 43, 44, 45, 46, 47, 48, 49, 60, 62, 64 and 76.

15. The oligonucleotide of claim 14, selected from the group consisting of Sequence ID Nos: 42, 43, 60, 62 and 64.

16. An oligonucleotide between 15 and 30 nucleotides in length, inclusive, that is fully complementary to and hybridizes with a sequence selected from the group consisting of Sequence ID Nos: 106, 107, 108 and 109.

17. An oligonucleotide between 15 and 30 nucleotides in length, inclusive, that specifically hybridizes in a human cell with a complementary sequence of a MRP gene and allelic variants thereof selected from the group consisting of Sequence ID Nos: 42, 43, 44, 45, 46, 47, 48, 49, 60, 62, 64 and 76.

18. The oligonucleotide of claim 17, selected from the group consisting of Sequence ID Nos: 42, 43, 60, 62 and 64.

19. The oligonucleotide of claim 17, which is between 17 and 27 nucleotides in length, inclusive.

20. The oligonucleotide of claim 17, which is phosphorothioate-modified.

21. An oligonucleotide for inhibiting expression of the multidrug resistance phenotype, having a sequence selected from the group consisting of Sequence ID Nos: 5, 27, 28, 88, 89, 90 and 91.

22. An oligonucleotide between 17 and 30 nucleotides in length, inclusive, having a sequence that specifically hybridizes in a human cell with a complementary sequence of a human MDR1 gene and allelic variants thereof to inhibit expression of a multidrug resistance phenotype exhibited by said cell, said complementary sequence having the sequence of Sequence ID No: 102.

23. The oligonucleotide of claim 22, which is between 17 and 26 nucleotides in length, inclusive.

24. The oligonucleotide of claim 22, which is phosphorothioate-modified.

25. The oligonucleotide of claim 22, which specifically hybridizes to said MDR1 gene, consisting of a sequence selected from the group of Sequence ID Nos: 25, 26, 27, 28, 29, 30, 31, 32, 33 and 34.

26. The oligonucleotide of claim 22, selected from the group consisting of Sequence ID Nos: 25, 26, 27, 28, 29, 30, 31 and 32.

27. An oligonucleotide between 15 and 26 nucleotides in length, inclusive, said oligonucleotide having a sequence that is fully complementary to and hybridizes with Sequence ID No: 102.

28. An oligonucleotide between 15 and 26 nucleotides in length, inclusive, said oligonucleotide having a sequence that specifically hybridizes with a complementary sequence of the MDR1 gene said oligonucleotide being selected from the group consisting of Sequence ID Nos: 25, 26, 27, 28, 29, 30, 31, 32, 33 and 34.

29. The oligonucleotide of claim 28, which is between 17 and 27 nucleotides in length, inclusive.

30. The oligonucleotide of claim 28, selected from the group consisting of Sequence ID Nos: 25, 26, 27, 28, 29, 30, 31 and 32.

31. The oligonucleotide of claim 28, which is phosphorothioate-modified.

32. The oligonucleotide of claim 28 which is at least 20 nucleotides in length.

* * * * *

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

CCCACGCCCC GGCGCTGTTC        20

( 2 ) INFORMATION FOR SEQ ID NO:2:

( i ) SEQUENCE CHARACTERISTICS:

(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:2:

GTGCTCAGCC CACGCCCCGG                    20

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:3:

GGCAAAGAGA GCGAAGCGGC                    20

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:4:

TGGCAAAGAG AGCGAAGCGG                    20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:5:

TCGAATGAGC TCAGGCTTCC                    20

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:6:

TCGAATGAGC TCAGGCTT                    18

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:7:

ACTCGAATGA GCTCAGGCTT CC               22

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:8:

AGCTCAGGCT TCCTGTGGCA                  20

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO (i v) ANTI-SENSE: YES (x i) SEQUENCE DESCRIPTION: SEQ ID NO:9:

CGAATGAGCT CAGGCT                      16

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: Not Relevant (i i) MOLECULE TYPE: DNA (genomic)

(i i i) HYPOTHETICAL: NO ( i v ) ANTI-SENSE: YES ( x i ) SEQUENCE DESCRIPTION: SEQ ID NO:10:

CCCTACCTCG CGCTCCTTGG AACGGC 26

( 2 ) INFORMATION FOR SEQ ID NO:11:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:11:

GCTCCCAGCT TTGCGTGCCC 20

( 2 ) INFORMATION FOR SEQ ID NO:12:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:12:

GCGCGCTCCG GGCAACATGG 20

( 2 ) INFORMATION FOR SEQ ID NO:13:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

CGCGCTCCGG GCAACATGGT CC 22

( 2 ) INFORMATION FOR SEQ ID NO:14:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

CGCGCTCCGG GCAACATG         18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:15:

CTCCGGGCAA CATGGTCC         18

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:16:

TGCTTCCTCC CACCCACCGC         20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:17:

TCCTCCCACC CACCGCCCGC         20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:18:

TTCCTCCCAC CCACCGCCCG         20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:19:

```
CTTCCTCCCA CCCACCGCCC                    20
```

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:20:

```
GCTTCCTCCC ACCCACCGCC                    20
```

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:21:

```
TCTGGACTTT GCCCGCCGCC                    20
```

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:22:

```
TTCTGGACTT TGCCCGCCGC                    20
```

( 2 ) INFORMATION FOR SEQ ID NO:23:

( i ) SEQUENCE CHARACTERISTICS:
        ( A ) LENGTH: 20 base pairs (B) TYPE: nucleic acid
            (C) STRANDEDNESS: single
            (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:23:

GTTCTGGACT TTGCCCGCCG                    20

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:24:

CGTTCTGGAC TTTGCCCGCC                    20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:25:

GCTCCTCCAT TGCGGTCCCC                    20

(2) INFORMATION FOR SEQ ID NO:26:

(i) SEQUENCE CHARACTERISTICS:
            (A) LENGTH: 22 base pairs
            (B) TYPE: nucleic acid
            (C) STRANDEDNESS: single
            (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:26:

GCTCCTCCAT TGCGGTCCCC TT                 22

(2) INFORMATION FOR SEQ ID NO:27:

(i) SEQUENCE CHARACTERISTICS:
            (A) LENGTH: 25 base pairs
            (B) TYPE: nucleic acid
            (C) STRANDEDNESS: single
            (D) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:27:

TCTTTGCTCC TCCATTGCGG TCCCC    25

( 2 ) INFORMATION FOR SEQ ID NO:28:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:28:

TTTGCTCCTC CATTGCGGTC CCC    23

( 2 ) INFORMATION FOR SEQ ID NO:29:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:29:

TCCTCCATTG CGGTCCCC    18

( 2 ) INFORMATION FOR SEQ ID NO:30:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:30:

CTCCATTGCG GTCCCCTT    18

( 2 ) INFORMATION FOR SEQ ID NO:31:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:31:

CTCCATTGCG GTCCCC         16

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:32:

CCATTGCGGT CCCCTTCA       18

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:33:

GCTCCTCCAT TGCGGTCC       18

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:34:

CCTCCATTGC GGTCCCCTTC     20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:35:

GCAACCAGCA CCCCAGCACC                    20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:36:

GCAGCAACCA GCACCCCAGC                    20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:37:

TGCCCACCAG AGCCAGCGTC                    20

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:38:

GCCTCCTTTG CTGCCCTCAC GA                 22

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:39:

CCAGGGCTTC TTGGACAACC TA                 22

(2) INFORMATION FOR SEQ ID NO:40:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:40:

```
GCGGGAGGTG AGTCACTGTC TCC                    23
```

( 2 ) INFORMATION FOR SEQ ID NO:41:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:41:

```
GGAGACAGTG ACTCACCTCC CGC                    23
```

( 2 ) INFORMATION FOR SEQ ID NO:42:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:42:

```
CGGCGGCGGC GGCGCAGGGA GCCGGG                 26
```

( 2 ) INFORMATION FOR SEQ ID NO:43:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:43:

```
CGGTGGCGCG GGCGGCGGCG GGCACC                 26
```

( 2 ) INFORMATION FOR SEQ ID NO:44:

( i ) SEQUENCE CHARACTERISTICS:
    ( A ) LENGTH: 20 base pairs
    ( B ) TYPE: nucleic acid (C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:44:

GCGGGTCGGA GCCATCGGCG    20

(2) INFORMATION FOR SEQ ID NO:45:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:45:

GAGCGGGTCG GAGCCATCGG    20

(2) INFORMATION FOR SEQ ID NO:46:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:46:

AGAGCGGGTC GGAGCCATCG    20

(2) INFORMATION FOR SEQ ID NO:47:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:47:

CCAGAGCGGG TCGGAGCCAT    20

(2) INFORMATION FOR SEQ ID NO:48:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:48:

CTGCGGCCCG GAAAACATCA                    20

(2) INFORMATION FOR SEQ ID NO:49:

(i) SEQUENCE CHARACTERISTICS:
   (A) LENGTH: 20 base pairs
   (B) TYPE: nucleic acid
   (C) STRANDEDNESS: single
   (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:49:

CGGTGATGCT GTTCGTGCCC                    20

(2) INFORMATION FOR SEQ ID NO:50:

(i) SEQUENCE CHARACTERISTICS:
   (A) LENGTH: 20 base pairs
   (B) TYPE: nucleic acid
   (C) STRANDEDNESS: single
   (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:50:

CGTGCCCCCG CCGTCTTTGA                    20

(2) INFORMATION FOR SEQ ID NO:51:

(i) SEQUENCE CHARACTERISTICS:
   (A) LENGTH: 20 base pairs
   (B) TYPE: nucleic acid
   (C) STRANDEDNESS: single
   (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:51:

TCGTGCCCCC GCCGTCTTTG                    20

(2) INFORMATION FOR SEQ ID NO:52:

(i) SEQUENCE CHARACTERISTICS:
   (A) LENGTH: 20 base pairs
   (B) TYPE: nucleic acid
   (C) STRANDEDNESS: single
   (D) TOPOLOGY: Not Relevant (ii) MOLECULE TYPE: DNA (genomic)

(iii) HYPOTHETICAL: NO (iv) ANTI-SENSE: YES ( x i ) SEQUENCE DESCRIPTION: SEQ ID NO:52:

TTCGTGCCCC CGCCGTCTTT                    20

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:53:

GTTCGTGCCC CCGCCGTCTT                    20

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:54:

TGTTCGTGCC CCCGCCGTCT                    20

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:55:

CTGTTCGTGC CCCCGCCGTC                    20

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:56:

GCTGTTCGTG CCCCCGCCGT                    20

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:57:

TGCTGTTCGT GCCCCCGCCG          20

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:58:

ATGCTGTTCG TGCCCCCGCC          20

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:59:

GATGCTGTTC GTGCCCCCGC          20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:60:

GGGCCAGGCT CACGCGCTGC          20

( 2 ) INFORMATION FOR SEQ ID NO:61:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:61:

GCCCGGGCCA GGCTCACGCG           20

( 2 ) INFORMATION FOR SEQ ID NO:62:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:62:

CCCTGGACCG CTGACGCCCG           20

( 2 ) INFORMATION FOR SEQ ID NO:63:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:63:

CGCCCGTGAC CCCGTTCTCC           20

( 2 ) INFORMATION FOR SEQ ID NO:64:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:64:

GCGGGATGAT GATGGCGGCG           20

( 2 ) INFORMATION FOR SEQ ID NO:65:

( i ) SEQUENCE CHARACTERISTICS:
      ( A ) LENGTH: 20 base pairs
      ( B ) TYPE: nucleic acid
      ( C ) STRANDEDNESS: single (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:65:

CGGGATGATG ATGGCGGCGA 20

(2) INFORMATION FOR SEQ ID NO:66:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:66:

GGCGGGATGA TGATGGCGGC 20

(2) INFORMATION FOR SEQ ID NO:67:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:67:

GGGCGGGATG ATGATGGCGG 20

(2) INFORMATION FOR SEQ ID NO:68:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:68:

GGGGCGGGAT GATGATGGCG 20

(2) INFORMATION FOR SEQ ID NO:69:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:69:

AGGGGCGGGA TGATGATGGC 20

(2) INFORMATION FOR SEQ ID NO:70:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:70:

ATGGCGGCGA TGGGCGTGGC 20

(2) INFORMATION FOR SEQ ID NO:71:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:71:

GATGGCGGCG ATGGGCGTGG 20

(2) INFORMATION FOR SEQ ID NO:72:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:72:

TGATGGCGGC GATGGGCGTG 20

(2) INFORMATION FOR SEQ ID NO:73:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: YES ( x i ) SEQUENCE DESCRIPTION: SEQ ID NO:73:

ATGATGGCGG CGATGGGCGT    20

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:74:

GATGATGGCG GCGATGGGCG    20

( 2 ) INFORMATION FOR SEQ ID NO:75:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:75:

TGATGATGGC GGCGATGGGC    20

( 2 ) INFORMATION FOR SEQ ID NO:76:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:76:

CGATGCCGAC CTTTCTCC    19

( 2 ) INFORMATION FOR SEQ ID NO:77:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:77:

GCCCCACGAT GCCGACCTTT    20

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:78:

CGCCCCACGA TGCCGACCTT    20

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:79:

CCGCCCCACG ATGCCGACCT    20

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:80:

TCCGCCCCAC GATGCCGACC    20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:81:

TGGCGGTGGC TGCTGCTTTG    20

( 2 ) INFORMATION FOR SEQ ID NO:82:

( i ) SEQUENCE CHARACTERISTICS:

( A ) LENGTH: 20 base pairs
            ( B ) TYPE: nucleic acid
            ( C ) STRANDEDNESS: single
            ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:82:

GGATGGCGGT GGCTGCTGCT        20

( 2 ) INFORMATION FOR SEQ ID NO:83:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:83:

CGGATGGCGG TGGCTGCTGC        20

( 2 ) INFORMATION FOR SEQ ID NO:84:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:84:

CCGGTGGGCG ATGGTGAGGA CG        22

( 2 ) INFORMATION FOR SEQ ID NO:85:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:85:

TGTCTCCGCT TCTTCCTGCC        20

( 2 ) INFORMATION FOR SEQ ID NO:86:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:86:

GCTCCTCCAT TGCGG    15

( 2 ) INFORMATION FOR SEQ ID NO:87:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:87:

CCTCGGTCCC CCCTCGTCCC    20

( 2 ) INFORMATION FOR SEQ ID NO:88:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:88:

CCCCTGGCGT TACCTCCTCG TTTCT    25

( 2 ) INFORMATION FOR SEQ ID NO:89:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:89:

TTCGCCTGAT TTCCGCCTCC CGTCT    25

( 2 ) INFORMATION FOR SEQ ID NO:90:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: Not Relevant ( i i ) MOLECULE TYPE: DNA (genomic)

( i i i ) HYPOTHETICAL: NO (iv) ANTI-SENSE: YES (xi) SEQUENCE DESCRIPTION: SEQ ID NO:90:

CGGTCCGTTA TGTTCCTG 18

(2) INFORMATION FOR SEQ ID NO:91:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:91:

ACTCGCCTCC CACGTAGTGC TT 22

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:92:

CGTGCCCCTA CCTCGCGCTC CT 22

(2) INFORMATION FOR SEQ ID NO:93:

(i) SEQUENCE CHARACTERISTICS:
        (A) LENGTH: 24 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (xi) SEQUENCE DESCRIPTION: SEQ ID NO:93:

CCCTACCTCG CGCTCCTTGG AACG 24

(2) INFORMATION FOR SEQ ID NO:94:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: DNA (genomic)

(iii) HYPOTHETICAL: NO (iv) ANTI-SENSE: YES (ix) FEATURE:

( A ) NAME/KEY: misc_feature
( B ) LOCATION: 4TH POSITION
( D ) OTHER INFORMATION: "oligonucleotide"
Inosine substitution for thymidine gives perfect match
both binding sites"

( x i ) SEQUENCE DESCRIPTION: SEQ ID NO:94:

CCCNACCTCG CGCTCCTTGG AA     22

( 2 ) INFORMATION FOR SEQ ID NO:95:

( i ) SEQUENCE CHARACTERISTICS:
( A ) LENGTH: 24 base pairs
( B ) TYPE: nucleic acid
( C ) STRANDEDNESS: single
( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:95:

CGTGCCCCTA CCTCGCGCTC CTTG     24

( 2 ) INFORMATION FOR SEQ ID NO:96:

( i ) SEQUENCE CHARACTERISTICS:
( A ) LENGTH: 18 base pairs
( B ) TYPE: nucleic acid
( C ) STRANDEDNESS: single
( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:96:

CGTGCCCCTA CCTCGCGC     18

( 2 ) INFORMATION FOR SEQ ID NO:97:

( i ) SEQUENCE CHARACTERISTICS:
( A ) LENGTH: 18 base pairs
( B ) TYPE: nucleic acid
( C ) STRANDEDNESS: single
( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:97:

TCCCGACCTC GCGCTCCT     18

( 2 ) INFORMATION FOR SEQ ID NO:98:

( i ) SEQUENCE CHARACTERISTICS:
( A ) LENGTH: 22 base pairs
( B ) TYPE: nucleic acid
( C ) STRANDEDNESS: single
( D ) TOPOLOGY: Not Relevant ( i i ) MOLECULE TYPE: DNA (genomic)

( i i i ) HYPOTHETICAL: NO ( i v ) ANTI-SENSE: YES ( i x ) FEATURE:
    ( A ) NAME/KEY: misc_feature
    ( B ) LOCATION: 4TH POSITION
    ( D ) OTHER INFORMATION: Substitution of guanine with
        inosine gives a perfect match with both binding sites.

( x i ) SEQUENCE DESCRIPTION: SEQ ID NO:98:

CCCNACCTCG CGCTCCTTGG AA    22

( 2 ) INFORMATION FOR SEQ ID NO:99:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:99:

CCATCCCGAC CTCGCGCTCC TTGG    24

( 2 ) INFORMATION FOR SEQ ID NO:100:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:100:

CCATCCCGAC CTCGCGCTCC TTGGAA    26

( 2 ) INFORMATION FOR SEQ ID NO:101:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: Not Relevant ( i i ) MOLECULE TYPE: DNA (genomic)

( i i i ) HYPOTHETICAL: NO ( i v ) ANTI-SENSE: YES ( i x ) FEATURE:
        ( A ) NAME/KEY: misc_feature
        ( B ) LOCATION: 4TH POSITION
        ( D ) OTHER INFORMATION: This variant sequence contains an
            inosine base substituted at the fourth position where
            the single base variation between SEQ ID:94 and
            SEQ ID NO:98 exists.

( x i ) SEQUENCE DESCRIPTION: SEQ ID NO:101:

CCCNACCTCG CGCTCCTTGG    20

( 2 ) INFORMATION FOR SEQ ID NO:102:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:102:

```
TGAAGGGGCA AGCAATGGAG GAGCAAAGAA GAAGAACT        38
```

( 2 ) INFORMATION FOR SEQ ID NO:103:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:103:

```
GGAAGCCTGA GCTCATTCGA GTAGC        25
```

( 2 ) INFORMATION FOR SEQ ID NO:104:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:104:

```
AGGGGCACGC AAAGCTGGGA GCT        23
```

( 2 ) INFORMATION FOR SEQ ID NO:105:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:105:

```
GGACCATGTT GCCCGGAGCG CGCA        24
```

( 2 ) INFORMATION FOR SEQ ID NO:106:

( i ) SEQUENCE CHARACTERISTICS:
    ( A ) LENGTH: 39 base pairs
    ( B ) TYPE: nucleic acid
    ( C ) STRANDEDNESS: single ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:106:

GCCACGCCCA  TCGCCGCCAT  CATCATCCCG  CCCCTTGGC        39

( 2 ) INFORMATION FOR SEQ ID NO:107:

( i ) SEQUENCE CHARACTERISTICS:
         ( A ) LENGTH: 70 base pairs
         ( B ) TYPE: nucleic acid
         ( C ) STRANDEDNESS: single
         ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:107:

CGGACAGAGA  TTGGCGAGAA  GGGCGTGAAC  CTGTCTGGGG  GCCAGAAGCA    50

GCGCGTGAGC  CTGGCCCGGG      70

( 2 ) INFORMATION FOR SEQ ID NO:108:

( i ) SEQUENCE CHARACTERISTICS:
         ( A ) LENGTH: 45 base pairs
         ( B ) TYPE: nucleic acid
         ( C ) STRANDEDNESS: single
         ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:108:

TCCACGACCT  GATGATGTTT  TCCGGGCCGC  AGATCTTAAA  GTTGC      45

( 2 ) INFORMATION FOR SEQ ID NO:109:

( i ) SEQUENCE CHARACTERISTICS:
         ( A ) LENGTH: 92 base pairs
         ( B ) TYPE: nucleic acid
         ( C ) STRANDEDNESS: single
         ( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:109:

GCCAGCACAG  AGCAGGAGCA  GGATGCAGAG  GAGAACGGGG  TCACGGGCGT    50

CAGCGGTCCA  GGGAAGGAAG  CAAAGCAAAT  GGAGAATGGG  AT           92

( 2 ) INFORMATION FOR SEQ ID NO:110:

( i ) SEQUENCE CHARACTERISTICS:
         ( A ) LENGTH: 20 base pairs
         ( B ) TYPE: nucleic acid
         ( C ) STRANDEDNESS: single (D) TOPOLOGY: Not Relevant (i i) MOLECULE TYPE: DNA (genomic)

(i i i) HYPOTHETICAL: NO (i v) ANTI-SENSE: YES (i x) SEQUENCE DESCRIPTION: SEQ ID NO:110:

TAGCCACATGGCCCCAGGAA 20

(2) INFORMATION FOR SEQ ID NO: 111:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (i i) MOLECULE TYPE: DNA (genomic)

(i i i) HYPOTHETICAL: NO (i v) ANTI-SENSE: YES (i x) SEQUENCE DESCRIPTION: SEQ ID NO: 111:

ACTGACTTGCCCCACGGCCA 20

(2) INFORMATION FOR SEQ ID NO: 112:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (i i) MOLECULE TYPE: DNA (genomic)

(i i i) HYPOTHETICAL: NO (i v) ANTI-SENSE: YES (i x) SEQUENCE DESCRIPTION: SEQ ID NO:112:

CCAAAGGGCAAAGGGCAAGG 20

(2) INFORMATION FOR SEQ ID NO: 113:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (i i) MOLECULE TYPE: DNA (genomic)

(i i i) HYPOTHETICAL: NO (i v) ANTI-SENSE: YES (i x) SEQUENCE DESCRIPTION: SEQ ID NO: 113:

GTACCTTACCTTTTATCTGG 20

(2) INFORMATION FOR SEQ ID NO: 114:

(i) SEQUENCE CHARACTERISTICS:
(A) LENGTH: 20 base pairs
(B) TYPE: nucleic acid
(C) STRANDEDNESS: single
(D) TOPOLOGY: Not Relevant (i i) MOLECULE TYPE: DNA (genomic)

( i i i ) HYPOTHETICAL: NO ( i v ) ANTI-SENSE: YES ( i x ) SEQUENCE DESCRIPTION: SEQ ID NO: 114:

TGCCCCTACCTCGCGCTCCT 20